United States Patent
Jordan

(10) Patent No.: US 7,316,820 B2
(45) Date of Patent: *Jan. 8, 2008

(54) MIXTURE FOR TRANSDERMAL DELIVERY OF LOW AND HIGH MOLECULAR WEIGHT COMPOUNDS

(75) Inventor: Frederick L. Jordan, Santa Ana, CA (US)

(73) Assignee: JRX Biotechnology, Inc., Irvine, CA (US)

( * ) Notice: Subject to any disclaimer, the term of this patent is extended or adjusted under 35 U.S.C. 154(b) by 3 days.

This patent is subject to a terminal disclaimer.

(21) Appl. No.: 11/411,293

(22) Filed: Apr. 26, 2006

(65) Prior Publication Data

US 2006/0188531 A1 Aug. 24, 2006

Related U.S. Application Data

(63) Continuation of application No. 10/856,567, filed on May 28, 2004, which is a continuation-in-part of application No. 10/789,836, filed on Feb. 27, 2004, which is a continuation of application No. 10/183,764, filed on Jun. 25, 2002, now Pat. No. 6,759,056, which is a continuation of application No. 09/350,043, filed on Jul. 8, 1999, now Pat. No. 6,946,144, said application No. 10/856,567.

(60) Provisional application No. 60/092,061, filed on Jul. 8, 1998, now abandoned, provisional application No. 60/510,615, filed on Oct. 10, 2003, now abandoned.

(51) Int. Cl.
*A61K 9/14* (2006.01)
*A61K 38/00* (2006.01)
*A61K 31/56* (2006.01)
*A01N 31/00* (2006.01)

(52) U.S. Cl. ............... 424/489; 424/742; 424/776; 514/1; 514/169

(58) Field of Classification Search ............ None
See application file for complete search history.

(56) References Cited

U.S. PATENT DOCUMENTS

| | | |
|---|---|---|
| 5,318,960 A | 6/1994 | Toppo |
| 5,431,924 A | 7/1995 | Ghosh et al. |
| 5,472,713 A | 12/1995 | Fein et al. |
| 5,571,671 A | 11/1996 | Potter |
| 5,614,212 A | 3/1997 | D'Angelo et al. |
| 5,665,378 A | 9/1997 | Davis et al. |
| 5,708,038 A | 1/1998 | Davis |
| 5,716,625 A | 2/1998 | Hahn et al. |
| 5,744,368 A | 4/1998 | Goldgaber et al. |
| 5,837,853 A | 11/1998 | Takashima et al. |
| 5,840,746 A | 11/1998 | Ducharme et al. |
| 5,849,334 A | 12/1998 | Rivlin |
| 5,861,268 A | 1/1999 | Tang et al. |
| 5,885,597 A | 3/1999 | Botknecht et al. |
| 5,891,651 A | 4/1999 | Roche et al. |
| 5,891,857 A | 4/1999 | Holt et al. |
| 5,958,384 A | 9/1999 | Holick |
| 6,103,246 A | 8/2000 | Tisdale et al. |
| 6,444,234 B1 | 9/2002 | Kirby et al. |
| 6,759,056 B2 * | 7/2004 | Jordan .................. 424/449 |
| 6,787,152 B2 | 9/2004 | Kirby et al. |
| 6,946,144 B1 * | 9/2005 | Jordan .................. 424/449 |
| 2003/0104040 A1 | 6/2003 | Kirby et al. |
| 2004/0170676 A1 * | 9/2004 | Jordan .................. 424/449 |
| 2004/0202709 A1 | 10/2004 | Kirby et al. |
| 2005/0019384 A1 * | 1/2005 | Jordan .................. 424/449 |
| 2006/0188532 A1 * | 8/2006 | Jordan .................. 424/400 |
| 2006/0193901 A1 * | 8/2006 | Jordan .................. 424/448 |

FOREIGN PATENT DOCUMENTS

| | | |
|---|---|---|
| WO | WO 92/08470 | 5/1992 |
| WO | WO 97/09992 A1 | 3/1997 |
| WO | WO 98/03163 | 1/1998 |
| WO | WO 98/33474 | 8/1998 |
| WO | WO 98/34629 | 8/1998 |

OTHER PUBLICATIONS

Aloe Laboratories. Manufacturing Procedures. Product: Regular Traditional Hand Fillet Aloe Vera Juice: 1 page.
Amadio, et al. 1993. Nonsteroidal anti-inflammatory drugs. *Postgraduate Medicine*, 93(4):73-97.
Barel and Clarys. 1995. Study of the Stratum Corneum Function by Transepidermal Water Loss Measurements: Comparison between Two Commercial Instruments. *Skin Pharmacol*, 8:186-195.
Biomedical Information Services Ltd. 1996. Inspection Criteria. General Standard for Testing Purity of Aloe Vera: 7 pages.
Bronaugh and Collier. 1991. In Vitro Percutaneous Absorption Studies:Principle, Fundamentals, and Applications, eds., Bronaugh and Malibach, Boca Rator, Fl. CRC Press, pp. 237-241.
Chattem Inc. 1999. Packaging-Flexall QuickGel.
Cohen, et al. 1992. Wound Healing/Biochemical and Clinical Aspects, 1st ed. WB Saunders, Philadelphia.
Collier et al. 1989. Maintenance of Skin Viability during in Vitro Percutaneous Absorption/Metabolism Studies. *Toxicology and Applied Pharmacology*, 99:522-533.
Croda, "Guide to specialty ingredients for the personal care industry," pp. i-iii and 1-42 (2000).
Cummings, et al., "A natural alternative: Jojoba esters are a new category of naturally derived, oil free emollients that offer good properties for a wide variety of cosmetic products," SPC Asia, (May 1999): 4 pages.
Cummings, et al., "In a nutshell,"; 3 pages.

(Continued)

Primary Examiner—Johann Richter
Assistant Examiner—Konata M. George
(74) Attorney, Agent, or Firm—Knobbe Martens Olson & Bear LLP

(57) ABSTRACT

The present invention relates to the discovery of a transdermal delivery system that can deliver high molecular weight pharmaceuticals and cosmetic agents to skin cells. A novel transdermal delivery system with therapeutic and cosmetic application and methods of use of the foregoing is disclosed.

188 Claims, No Drawings

OTHER PUBLICATIONS

Downing et al. 1993. Dermatology in General Medicine. Fitzpatrick, et al., eds., pp. 210-221.
Esoteric Oils (Pty), "Macadamia oil for massage therapy and to help moisturize the skin," http:///www.essentialoils.co.za/macadamia_oil.htm, pp. 1-3, (May 5, 2004).
FLORAESTERS® International Flora Technologies. Product Specification for FLORAESTERS® 20: 1 page.
FLORAESTERS® International Flora Technologies. Product Specification for FLORAESTERS® 30: 1 page.
FLORAESTERS® International Flora Technologies. Product Specification for FLORAESTERS® 60: 1 page
FLORAESTERS® International Flora Technologies. Product Specification for FLORAESTERS® 70: 1 page.
FLORAESTERS® International Flora Technologies. Product Specification for FLORASOLVS® PEG-10 Sunflower: 1 page.
FLORAESTERS® International Flora Technologies. Product Specification for FLORASUN® 90, Refined, Bleached, Winterized, Deodorized: 1 page.
FLORAESTERS® International Flora Technologies. Product Specification for FLORAESTERS® IPJ: 1 page.
FLORAESTERS® International Flora Technologies. Product Specification for FLORAESTERS® HIPJ: 1 page.
FLORAESTERS® International Flora Technologies. Product Specification for FLORABEADS®, JOJOBA 40/60: 1 page.
FLORAESTERS® International Flora Technologies. Product Specification for FLORABEADS®, JOJOBA White 60/100: 1 page.
FLORAESTERS® International Flora Technologies. Product Specification for FLORASOLVS® PEG-80 Jojoba: 1 page.
FLORAESTERS® International Flora Technologies. Product Specification for FLORASOLVS® PEG-120 Jojoba: 1 page.
FLORAESTERS® International Flora Technologies. Product Specification for FLORAESTERS® Jojoba Oil, Pasteurized, Not Refined: 1 page.
FLORAESTERS® International Flora Technologies. Product Specification for FLORAESTERS® 15: 1 page.
FLORAESTERS® International Flora Technologies. Product Specification for FLORABEADS®, JOJOBA 28/60, 1 of 2: 1 page.
FLORAESTERS® International Flora Technologies. Product Specification for FLORABEADS®, JOJOBA 28/60, 2 of 2: 1 page.

Grindlay and Reynold. 1986. The Aloe Vera Phenomenon: A Review of the Properties and Modern Uses of the Leaf Parenchyma Gel. *J. of Ethnopharmacology*, 16:117-151.
Hart, et al. 1988. Two Functionally and Chemically Distinct Immunomodulatory Compounds in the Gel of Aloe Vera. *J. of Ethnopharmacology*, 23:61-71.
Hirata, et al. 1977. Biologically Active Constituents of Leaves and Roots of Aloe Arborescens var. Natalensis. *Z. Naturforsch*, 32c:731-734.
http://www.botanical.com/botanical/mgmh/f/gtanki31.html.
http://www.natplus.com/products/productNumber=7124.
International Aloe Science Council, Inc. The Datasheet-100% Pure Aloe Vera: 1 page.
International Search Report from PCT/US99/15409 dated Jan. 13, 2000.
Melaslow™, Brightening Cream with Melaslow™, SC-306, product formula: 2 pages.
Melaslow™, Skin Lightening Age Spot Treatment, product specification and claim substantiation: 2 pages.
Nelson, et al. 1991. Mid-Infrared Laser Ablation of Stratum Corneum Enhanves in Vitro Percutaneous Transport of Drugs. *The Society for Investigative Dermatology, Inc*.:878-879.
O'Malley, P. et al., "Emu Products, Increasing Production and Profitability," *Rural Industruies and Development Corporation*, pp. i-110, Dec. 1999.
Ponec, M. 1994, Epidermal Lipids in Vivo. *The Keratinocyte Handbook*, Leigh, et al., eds., pp. 351-363.
Sederma, Etioline, product brochure, pp. 1-16 (Oct. 1996).
Sederma, Ichtyocollagene, product brochure, pp. 1-19 (Aug. 1993).
Sederma, Matrixyl "The physiological reconstruction of the matrix structures of the dermis to reduce deep and medium wrinkles: tested in vivo on a panel of 35 subjects during 2-4-6 months," product brochure, synopsis and pp. 1-44 (Sep. 1999).
Sederma, Melaslow™ "Lightens the complexion/Decreases age spots," product brochure, overview and pp. 1-28 (Dec. 2000).
Taguchi, et al., "Enhancement of propylene glycol distribution in the skin by high purity *cis*-unsaturated fatty acids with different alkyl chain lengths having different double bond position," Biol. Pharm. Bull., vol. 22, No. 4, pp. 407-411 (1999).
Woodin, L. 1993. Cutting Postop Pain. *RN*, Aug. 26-33.

\* cited by examiner

MIXTURE FOR TRANSDERMAL DELIVERY OF LOW AND HIGH MOLECULAR WEIGHT COMPOUNDS

CROSS-REFERENCE TO RELATED APPLICATIONS

This application claims priority to and is a continuation of U.S. patent application Ser. No. 10/856,567, filed May 28, 2004, which claims priority to and is a continuation-in-part of U.S. patent application Ser. No. 10/789,836, filed Feb. 27, 2004, which claims priority to and is a continuation of U.S. patent application Ser. No. 10/183,764, filed Jun. 25, 2002, now issued as U.S. Pat. No. 6,759,056, which claims priority to and is a continuation of U.S. application Ser. No. 09/350,043, filed Jul. 8, 1999, now issued as U.S. Pat. No. 6,946,144, which claims priority to U.S. Provisional Application No. 60/092,061, filed Jul. 8, 1998 (now abandoned). This application also claims priority to U.S. Provisional Application No. 60/510,615, filed Oct. 10, 2003 (now abandoned). All of the above-referenced applications are hereby expressly incorporated by reference in their entireties.

FIELD OF THE INVENTION

The present invention relates to the discovery of several formulations of a transdermal delivery system that deliver low and high molecular weight compounds, particularly drugs and cosmetic agents to a subject. A novel transdermal delivery system with therapeutic and cosmetic application is disclosed.

BACKGROUND OF THE INVENTION

The skin provides a protective barrier against foreign materials and infection. In mammals this is accomplished by forming a highly insoluble protein and lipid structure on the surface of the corneocytes termed the cornified envelope (CE). (Downing et al., *Dermatology in General Medicine*, Fitzpatrick, et al., eds., pp. 210-221 (1993), Ponec, M., *The Keratinocyte Handbook*, Leigh, et al., eds., pp. 351-363 (1994)). The CE is composed of polar lipids, such as ceramides, sterols, and fatty acids, and a complicated network of cross-linked proteins; however, the cytoplasm of stratum corneum cells remains polar and aqueous. The CE is extremely thin (10 microns) but provides a substantial barrier. Because of the accessibility and large area of the skin, it has long been considered a promising route for the administration of drugs, whether dermal, regional, or systemic effects are desired.

A topical route of drug administration is sometimes desirable because the risks and inconvenience of parenteral treatment can be avoided; the variable absorption and metabolism associated with oral treatment can be circumvented; drug administration can be continuous, thereby permitting the use of pharmacologically active agents with short biological half-lives; the gastrointestinal irritation associated with many compounds can be avoided; and cutaneous manifestations of diseases can be treated more effectively than by systemic approaches.

Most transdermal delivery systems achieve epidermal penetration by using a skin penetration enhancing vehicle. Such compounds or mixtures of compounds are known in the art as "penetration enhancers" or "skin enhancers". While many of the skin enhancers in the literature enhance transdermal absorption, several possess certain drawbacks in that (i) some are regarded as toxic; (ii) some irritate the skin; (iii) some have a thinning effect on the skin after prolonged use; (iv) some change the intactness of the skin structure resulting in a change in the diffusability of the drug; and (v) all are incapable of delivering high molecular weight pharmaceuticals and cosmetic agents. Clearly there remains a need for safe and effective transdermal delivery systems that can administer a wide-range of pharmaceuticals and cosmetic agents.

BRIEF SUMMARY OF THE INVENTION

Aspects of the invention concern transdermal delivery systems comprised of an ethoxylated lipid. Some formulations are used to deliver pharmaceuticals, therapeutic compounds, and cosmetic agents of various molecular weights. In several embodiments, the transdermal delivery system comprises a unique formulation of penetration enhancer (an ethoxylated oil or fatty acid, fatty alcohol, or fatty amine therein having 10-19 ethoxylations per molecule) that delivers a wide range of pharmaceuticals and cosmetic agents having molecular weights of less than 100 daltons to greater than 500,000 daltons. For example, embodiments of the transdermal delivery system include formulations that deliver a therapeutically effective amount of non-steroidal anti-inflammatory drugs (NSAIDs), capsaicin or Boswellin-containing pain-relief solutions, other drugs or chemicals, dyes, low and high molecular weight peptides (e.g., collagens or fragments thereof), hormones, nucleic acids, antibiotics, vaccine preparations, and immunogenic preparations. Methods of making the transdermal delivery systems described herein and methods of using said compositions (e.g., the treatment and prevention of undesired human conditions or diseases or cosmetic applications) are embodiments.

Some transdermal delivery system formulations are composed of a penetration enhancer that comprises an ethoxylated lipid (e.g., an ethoxylated macadamia nut oil) and a delivered agent (e.g., an amino acid, peptide, nucleic acid, protein, hydrolyzed protein, nutriceutical, chemical, or drug). An alcohol and/or water and/or an aqueous adjuvant can be mixed with the penetration enhancer to improve the solubility and/or transport of a particular delivered agent. In some embodiments, the aqueous adjuvant is a plant extract from the family of *Liliaceae*, such as *Aloe Vera*. The ethoxylated lipid that can be used in the formulations described herein can be a vegetable, nut, animal, or synthetic oil or fatty acid, fatty alcohol, or fatty amine therein having at least 10, 11, 12, 13, 14, 15, 16, 17, 18, 19, or more ethoxylations per molecule. Preferred oils include macadamia nut oil or meadowfoam (*limnanthes alba*).

In some aspects of the invention, about 0.1% to greater than 99.0% by weight or volume is ethoxylated lipid, preferably an oil or component thereof. It should be understood that when an oil is ethoxylated, one or more of the components of the oil are ethoxylated (e.g., fatty acids, fatty alcohols, and/or fatty amines) and it is generally recognized in the field that an average number of ethoxylations for the oil and components is obtained and therefore provided. That is, the measured composition is the algebraic sum of the compositions of the species in the mix. Other embodiments of the invention include the transdermal delivery system described above, wherein about 0.1% to 15% by weight or volume is alcohol or 0.1% to 15% is water or both, or wherein about 0.1% to 85% by weight or volume is water or *Aloe Vera* or another aqueous adjuvant.

Alcohol, water, and other aqueous adjuvants are not present in some formulations of the transdermal delivery system described herein. It has been discovered that some delivered agents (e.g., steroids) are soluble and stable in ethoxylated oil in the absence of alcohol or water and some delivered agents are soluble and stable in ethoxylated oil/alcohol emulsions, ethoxylated oil/water emulsions, ethoxylated oil/alcohol/water emulsions, and ethoxylated oil/alcohol/water/*Aloe Vera* emulsions. In particular, it was found that a particular *Aloe Vera*, alcohol, or water mixture was not essential to obtain a transdermal delivery system provided that an appropriately ethoxylated oil was mixed with the delivered agent. That is, the alcohol, water, and *Aloe Vera* can be removed from the formulation by using a light oil (e.g., macadamia nut oil) that has been ethoxylated to approximately 10-19 ethoxylations/molecule, desirably 11-19 ethoxylations/molecule, more desirably 12-18 ethoxylations/molecule, still more desirably 13-17 ethoxylations/molecule, preferably 14-16 ethoxylations/molecule and most preferably 15 or 16 ethoxylations/molecule. For example, some ethoxylated oils (e.g., macadamia nut oil containing 10, 11, 12, 13, 14, 15, 16, 17, 18, or 19 ethoxylations/molecule) can deliver low and high molecular weight peptides (e.g., collagen and fragments of collagen) or amino acids in the absence of alcohol and *Aloe Vera*. Some embodiments, however, have a ratio of ethoxylated lipid:alcohol:aqueous adjuvant selected from the group consisting of 1:1:4, 1:1:14, 3:4:3, and 1:10:25.

Desirably, the transdermal delivery systems described herein contain delivered agents that are molecules with a molecular weight of less than about 6,000 daltons. In some embodiments, the transdermal delivery systems described herein contain a delivered agent that is one or more of the compounds selected from the group consisting of capsaicin, Boswellin, non-steroidal anti-inflammatory drug (NSAID), collagen, hydrolyzed collagen, peptide, amino acids, nucleic acids, alpha hydroxy acid, or alpha keto acid or salts or esters of these acids. (See U.S. Patent Publication No. 20040043047A1, herein expressly incorporated by reference in its entirety). Other desirable delivered agents include peptides or nucleic acids encoding peptides that comprise the sequence LKEKK (SEQ. ID. No. 1), in particular, the peptides disclosed in U.S. Patent Publication No. 20020082196A1, herein expressly incorporated by reference in its entirety. Still more desirable delivered agents include Phenyloin, Valproic acid, Cyclosporin A, Nifedipine, Diltiazem, Verapamil HCl, and Amoldipine, which may be used to induce collagen synthesis. (See U.S. Patent Publication No. 20040052750A1, herein expressly incorporated by reference in its entirety). Other delivered agents include, for example, hepsyls, acyclovir or other antiviral compounds, steroids such as progesterone, estrogen, testosterone, androstiene, glucosamine, chondroitin sulfate, MSM, perfumes, melasin, antibiotics, nicotin, nicotine analogs, anti-nausea medicines, such as scopolamine, and insulin. In some embodiments, however, the delivered agent is a molecule with a molecular weight of greater than 6,000 daltons (e.g., a protein, a growth factor, or a collagen).

The transdermal delivery systems described herein can also include fragrances, creams, bases and other ingredients that stabilize the formulation, facilitate delivery, or protect the delivered agent from degradation (e.g., agents that inhibit DNAse, RNAse, or proteases). The formulations described herein are placed into a vessel that is joined to an applicator such that the active ingredients can be easily provided to a subject. Applicators include, but are not limited to, roll-ons, bottles, jars, tubes, sprayer, atomizers, brushes, swabs, gel dispensing devices, and other dispensing devices.

Several methods of using the transdermal delivery systems are also embodiments. For example, one approach involves a method of reducing pain or inflammation by using a transdermal delivery system that comprises an anti-inflammatory molecule (e.g., an NSAID or MSM) on a subject in need of a reduction of pain or inflammation. Monitoring the reduction in inflammation may also be desired as part of a rehabilitation program.

NSAIDs and other chemotherapeutic agents have also been shown to improve the health, welfare, or survival of subjects that have cancer or Alzheimer's disease. Accordingly, some embodiments concern methods of using transdermal delivery systems that comprise delivered agents (e.g., NSAIDs or other chemotherapeutic agents such as flurouracil) to treat or prevent cancer or hyperproliferative cell disorders (e.g., basal cell carcinoma or actinic keratosis.) For example, a method to improve the health, welfare, or survival of a subject that has cancer or Alzheimer's disease or a method of treating or preventing cancer or Alzheimer's disease in said subject can be conducted by using a transdermal delivery system that comprises a COX enzyme inhibitor and providing said transdermal delivery system to said subject.

Some formulations of transdermal delivery systems can be used to reduce oxidative stress to cells, tissues and the body of a subject. For example, a method to improve the health, welfare, or survival of a subject that is in need of a reduction in oxidative stress to a cell, tissue, or the body as a whole involves providing to said subject a transdermal delivery system that comprises an antioxidant such as ascorbic acid, tocopherol or tocotrienol or an anti-stress compound such as Bacocalmine (Bacopa Monniera Extract obtained from Sederma Laboratories). Methods of treating or preventing diseases or conditions associated with oxidative stress or vitamin deficiency and methods of reducing an oxidative stress or a vitamin deficiency in a subject in need thereof are also embodiments.

Other formulations of transdermal delivery system can be used to reduce psoriasis or eczema or a related condition or can be used to promote wound healing in a subject in need thereof. By one approach, a transdermal delivery system that comprises peptides that promote wound healing (e.g., peptides comprising the sequence LKEKK (SEQ. ID. No. 1), are provided to a subject in need of a treatment or reduction in psoriasis or eczema or a condition associated with psoriasis or eczema (e.g., allergies) or treatment of a wound.

Other formulations of transdermal delivery system can be used to relax the muscles of a subject. By one approach, a transdermal delivery system that comprises a compound that relaxes the muscles (e.g., chlorzoxazone or ibuprofen) is provided to a subject in need of a muscle relaxant. Accordingly methods of treating or preventing muscle soreness are embodiments.

Other formulations of transdermal delivery system can be used to raise the levels of a hormone in a subject in need thereof. By one approach, a transdermal delivery system that comprises a hormone (e.g., testosterone or estrogen or derivatives or functional analogues thereof) is provided to a subject in need thereof. Accordingly methods of treating or preventing a hormone deficiency or methods of increasing the level of a hormone in a subject using one of the transdermal delivery systems described herein are embodiments.

Other formulations of transdermal delivery system can be used to raise the levels of a growth factor in a subject in need thereof. By one approach, a transdermal delivery system that comprises a growth factor (e.g., a growth factor contained in Bioserum, which is obtainable through Atrium Biotechnologies of Quebec City, Canada) is provided to a subject in need thereof. In other embodiments, a transdermal delivery system comprising a peptide that comprises the sequence LKEKK (SEQ. ID. No. 1) is provided to a subject in need of an increase in a growth factor. Accordingly methods of treating or preventing a growth factor deficiency or methods of increasing the level of a growth factor in a subject using one of the transdermal delivery systems described herein are embodiments.

Other formulations of the transdermal delivery system described herein are used to brighten the skin, reduce age spots or skin discolorations, reduce stretch marks, reduce spider veins, or add dyes, inks, (e.g., tattoo ink), perfumes, or fragrances to the skin of a subject. In some embodiments, for example, transdermal delivery systems that comprise a compound that brightens the skin or reduces age spots or skin discolorations (e.g., Melaslow, a citrus-based melanin (tyrosinase) inhibitor obtainable from Revivre Laboratories of Singapore or Etioline, a skin brightener made from an extract from the *Mitracarpe* leaf obtainable from Krobell, USA), or a compound that reduces stretch marks (Kayuuputih Eucalyptus Oil, obtainable from Striad Laboratories) or add dyes, inks, (e.g., tattoo ink), perfumes, or fragrances are provided to the skin of a subject.

It has also been discovered that ethoxylated oil by itself, preferably *macadamia* nut oil having 10-20 ethoxylations/molecule (i.e., 10, 11, 12, 13, 14, 15, 16, 17, 18, or 19 ethoxylations/molecule), has therapeutic and cosmetic properties. For example, application of an ethoxylated oil (macadamia nut oil having 16 ethoxylations/molecule) was found to reduce stretch marks and spider veins on a subject in need thereof. Application of an ethoxylated oil (macadamia nut oil having 16 ethoxylations/molecule) to a burn (e.g., a sun burn or a skin burn obtained from over-heated metal) was found to significantly expedite recovery from the burn, oftentimes without blistering. Accordingly, some embodiments concern a transdermal delivery system comprising an ethoxylated oil (e.g., macadamia nut oil that was ethoxylated 10-19 ethoxylations per molecule, 11-19 per molecule, 12-18 ethoxylations per molecule, 13-17 ethoxylations per molecule, 14-16 ethoxylations per molecule, or 15 ethoxylations per molecule) and these compositions are used to reduce the appearance of stretch marks and spider veins or facilitate the recovery from burns of the skin.

In addition to the delivery of low and medium molecular weight delivered agents, several compositions that have high molecular weight delivered agents (e.g., collagens) and methods of use of such compositions are embodiments of the invention. Preferred formulations of the transdermal delivery system comprise a collagen (natural or synthetic) or fragment thereof at least 2, 4, 6, 8, 10, 12, 14, 16, 18, 20, 24, 30, 40, 50, 100, 250, 500, 1000, 1500, 2000, 2500, 3000, 5000, or more amino acids in length and these compositions are used to reduce wrinkles and fine lines on a subject.

For example, some embodiments concern a transdermal delivery system comprising an ethoxylated oil or an ethoxylated component thereof (e.g., macadamia nut oil that was ethoxylated 10-19 ethoxylations per molecule, 11-19 per molecule, 12-18 ethoxylations per molecule, 13-17 ethoxylations per molecule, 14-16 ethoxylations per molecule, or 15 ethoxylations per molecule) and a therapeutically effective amount of a collagen or fragment thereof (e.g., marine collagen). In some aspects of the invention, a transdermal delivery system comprising an ethoxylated oil and collagen also contains water and/or an alcohol and/or an aqueous adjuvant such as *Aloe Vera*.

In different embodiments of this transdermal delivery system, the collagen has a molecular weight less than, or equal to 6,000 daltons or greater than 6,000 daltons. Thus, in some embodiments, the collagen can have an approximate molecular weight as low as 2,000 daltons or lower. In other embodiments, the molecular weight is from about 300,000 daltons to about 500,000 daltons. Further, these transdermal delivery systems can have a therapeutically effective amount of collagen or fragment thereof by weight or volume that is 0.1% to 85.0%. The collagen can be any natural or synthetic collagen, for example, Hydrocoll EN-55, bovine collagen, human collagen, a collagen derivative, marine collagen, Solu-Coll, or Plantsol, recombinant or otherwise man made collagens or derivatives or modified versions thereof (e.g., protease resistant collagens). As above, an apparatus having a vessel joined to an applicator that houses the transdermal delivery system containing collagen is also an embodiment and preferred applicators or dispensers include a roll-on or a sprayer.

Accordingly, some of the embodied methods concern the reduction of wrinkles and or the improvement of skin tone by using a transdermal delivery system comprising an ethoxylated oil and a collagen and/or a fragment thereof. Some formulations to be used to reduce wrinkles and improve skin tone include an ethoxylated oil (e.g., macadamia nut oil that was ethoxylated 10-19 ethoxylations per molecule, 11-19 per molecule, 12-18 ethoxylations per molecule, 13-17 ethoxylations per molecule, 14-16 ethoxylations per molecule, or 15 ethoxylations per molecule) and a therapeutically effective amount of a collagen or fragment thereof (e.g., marine collagen) that is at least 2, 4, 6, 8, 10, 12, 14, 16, 18, 20, 24, 30, or 40 amino acids in length. Some formulations that can be used to practice the method above include a transdermal delivery system comprising an ethoxylated oil and collagen or fragment thereof, as described above, and, optionally, water and/or an alcohol and/or an aqueous adjuvant such as *Aloe Vera*. For example, by one approach, a method of reducing wrinkles or improving skin tone is practiced by identifying a subject in need thereof and providing said subject a transdermal delivery system, as described herein and, optionally, monitoring the subject for restoration or improvement of skin tone and the reduction of wrinkles.

DETAILED DESCRIPTION OF THE INVENTION

In the following disclosure, several transdermal delivery systems are described that can administer an effective amount of a pharmaceutical or cosmetic agent to the human body. Although embodiments of the invention can be used to administer low or high (or both low and high) molecular weight pharmaceuticals and cosmetic agents, preferred embodiments include transdermal delivery systems that can administer compounds having molecular weights greater than 6,000 daltons. One embodiment, for example, includes a transdermal delivery system that can administer a therapeutically effective amount of a non-steroidal anti-inflammatory drug (NSAID). Another embodiment concerns a transdermal delivery system having a novel pain-relief solution (e.g., a formulation comprising capsaicin or Boswellin or both). Another aspect of the invention involves a transdermal delivery system that can administer a collagen preparation (e.g., soluble collagens, hydrolyzed collagens, and fragments of collagen). Still more embodiments concern transdermal delivery systems that can administer nucleic acids, peptides, immunogenic preparations, hepsyls, acyclovir, ribavirin, or other antiviral compounds, steroids such as progesterone, estrogen, testosterone, androstiene, glucosamine, chondroitin sulfate, MSM, perfumes, melasin, antibiotics, and insulin. These examples are provided to demonstrate that embodiments of the invention can be used to transdermally deliver both low and high molecular weight compounds and it should be understood that many other molecules can be effectively delivered to the body, using the embodiments described herein, in amounts that are therapeutically, prophylactically, or cosmetically beneficial.

The embodied transdermal delivery systems described herein comprise a penetration enhancer that includes an ethoxylated lipid. It was discovered that ethoxylated lipids (e.g., ethoxylated oils) can be used as transdermal penetration enhancers in that they effectively transport low and high molecular weight compounds through the skin. It was also discovered that ethoxylated oils, by themselves, have therapeutic and cosmetic applications (e.g., the reduction of the appearance of spider veins and stretch marks or promoting expedited recovery from burns to the skin). It is also contemplated that ethoxylated fatty acids (e.g., palmitoleic acid or oleic acid) can be used in some embodiments (e.g., to fortify or supplement ethoxylated macadamia nut oil).

Although an ethoxylated lipid can be created in many ways, a preferred approach involves the reaction of ethylene oxide with a vegetable, nut (e.g., macadamia nut), animal, or synthetic oil. The hydrophilic component can be by virtue of the number of ethoxylations present on the lipid molecule. Additionally, an alcohol, a nonionic solubilizer or an emulsifier may be added to improve the solubility of the delivered agent or effectiveness or fluidity of the penetration enhancer. Suitable hydrophilic components include, but are not limited to, ethylene glycol, propylene glycol, dimethyl sulfoxide (DMSO), dimethyl polysiloxane (DMPX), oleic acid, caprylic acid, isopropyl alcohol, 1-octanol, ethanol (denatured or anhydrous), and other pharmaceutical grade or absolute alcohols.

Embodiments of the invention can also comprise an aqueous adjuvant. Aqueous adjuvants include, but are not limited to, water (distilled, deionized, filtered, or otherwise prepared), Aloe Vera juice, and other plant extracts such as chlorophyll or Spirulina. Thus, several embodiments of the invention have a penetration enhancer that includes a hydrophobic/hydrophilic component comprising an ethoxylated oil (e.g., macadamia nut oil, coconut oil, eucalyptus oil, synthetic oils, castor oil, glycerol, corn oil, jojoba oil, or emu oil) and may contain a hydrophilic component comprising an alcohol, a nonionic solubilizer, or an emulsifier (e.g., isopropyl alcohol) and/or, optionally, an aqueous adjuvant, such as water and/or Aloe Vera extract.

Other materials can also be components of a transdermal delivery system of the invention including fragrance, creams, ointments, colorings, and other compounds so long as the added component does not deleteriously affect transdermal delivery of the delivered agent. It has been found that the Aloe Vera, which allows for transdermal delivery of high molecular weight delivered agents, including collagen having an average molecular weight greater than 6,000 daltons, can be removed from the formulation if a light oil (e.g., macademia nut oil) that has been ethoxylated to the range of 10-19 ethoxylations/molecule is used. Formulations lacking Aloe Vera provide the unexpected benefit of efficient transdermal delivery, uniform application and quick penetration making these formulations superior to formulations that contain Aloe Vera.

Similarly, formulations of transdermal delivery systems that lack alcohol provide the unexpected benefit of efficient transdermal delivery, uniform application, and quick penetration without the drying or irritation brought about by the alcohol. Additionally, formulations lacking water or other aqueous adjuvants provide efficient transdermal delivery while maintaining the highest possible concentration of delivered agent and, also, provide for quick penetration without the skin-drying effects seen with some formulations that contain alcohol.

A molecule or a mixture of molecules (e.g., a pharmaceutical, chemical, or cosmetic agent) that are delivered to the body using an embodiment of a transdermal delivery system are termed "delivered agents". A delivered agent that can be administered to the body using an embodiment of the invention can include, for example, a protein or peptide, a sugar, a nucleic acid, a chemical, or a lipid. Desirable delivered agents include, but are not limited to, glycoproteins, enzymes, genes, drugs, and ceramides. Preferred delivered agents include collagens or fragments thereof, NSAIDS, capsaicin, and Boswellin. In some embodiments, a transdermal delivery system comprises a combination of any two of the aforementioned delivered agents. Other delivered agents include, for example, hepsyls, acyclovir or other antiviral compounds, steroids such as progesterone, estrogen, testosterone, androstiene, glucosamine, chondroitin sulfate, MSM, perfumes, melasin, antibiotics, insulin, nicotine, nicotine analogs, peptides, amino acids, nucleic acids, antiviral compounds, and peptidomimetics.

In addition to the aforementioned compositions, methods of making and using the embodiments of the invention are provided. In general, an embodiment of the invention is prepared by mixing a hydrophilic component with a hydrophobic component and an aqueous adjuvant. Depending on the solubility of the delivered agent, the delivered agent can be solubilized in either the ethoxylated oil, a hydrophobic, hydrophilic, or aqueous adjuvant or water prior to mixing. In addition to physical mixing techniques (e.g., magnetic stirring or rocker stirring) heat can be applied to help coalesce the mixture. Desirably, the temperature is not raised above 40° C.

Several formulations of transdermal delivery system are within the scope of aspects of the invention. One formulation comprises a ratio of hydrophilic component:hydrophobic component:aqueous adjuvant of 3:4:3. The amount of delivered agent that is incorporated into the penetration enhancer depends on the compound, desired dosage, and application. The amount of delivered agent in a particular formulation can be expressed in terms of percentage by weight, percentage by volume, or concentration. Several specific formulations of delivery systems are provided in the Examples described herein.

Methods of treatment and prevention of pain, inflammation, and human disease are also provided. In some embodiments, a transdermal delivery system comprising an NSAID, capsaicin, Boswellin or any combination thereof is provided to a patient in need of treatment, such as for relief of pain and/or inflammation. A patient can be contacted with the transdermal delivery system and treatment continued for a time sufficient to reduce pain or inflammation or inhibit the progress of disease.

Additionally, a method of reducing wrinkles, removing age spots, and increasing skin tightness and flexibility is provided. By this approach, a transdermal delivery system comprising a collagen or fragment thereof or melaslow or other skin brightening agent is provided to a patient in need, the patient is contacted with the transdermal delivery system, and treatment is continued for a time sufficient to restore a desired skin tone (e.g., reduce wrinkles, age spots, or restore skin brightness, tightness and flexibility). In the disclosure below, there is provided a description of several of the delivered agents that can be incorporated into the transdermal delivery systems described herein.

Delivered Agents

Many different delivered agents can be incorporated into the various transdermal delivery systems described herein and a non-exhaustive description of embodiments is provided in this section. While the transdermal delivery of molecules having a molecular weight in the vicinity of 6000 daltons has been reported, it has not been possible, until the present invention, to administer molecules of greater size transdermally. (See U.S. Pat. No. 5,614,212 to D'Angelo et al., herein expressly incorporated by reference in its entirety).

The described embodiments can be organized according to their ability to deliver a low or high molecular weight delivered agent. Low molecular weight molecules (e.g., a molecule having a molecular weight less than 6,000 daltons) can be effectively delivered using an embodiment of the invention and high molecular weight molecules (e.g., a molecule having a molecular weight greater than 6,000 daltons) can be effectively delivered using an embodiment of the invention. Desirably, a transdermal delivery system described herein provides a therapeutically or cosmetically beneficial amount of a delivered agent having a molecular weight of 50 daltons to less than 6,000 daltons. Preferably, however, a transdermal delivery system described herein provides a therapeutically or cosmetically beneficial amount of a delivered agent having a molecular weight of 50 daltons to 2,000,000 daltons or less. That is, a transdermal delivery system described herein, preferably, provides a delivered agent having a molecular weight of less than or equal to or greater than 50, 100, 200, 500, 1,000, 1,500, 2,000, 2,500, 3,000, 3,500, 4,000, 4,500, 5,000, 5,500, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 46,000, 47,000, 48,000, 49,000, 50,000, 51,000, 52,000, 53,000, 54,000, 55,000, 56,000, 57,000, 58,000, 59,000, 60,000, 61,000, 62,000, 63,000, 64,000, 65,000, 66,000, 67,000, 68,000, 69,000, 70,000, 75,000, 80,000, 85,000, 90,000, 95,000, 100,000, 125,000, 150,000, 175,000, 200,000, 225,000, 250,000, 275,000, 300,000, 350,000, 400,000, 450,000, 500,000, 600,000, 700,000, 800,000, 900,000, 1,000,000, 1,500,000, 1,750,000, and 2,000,000 daltons.

In one aspect, a low molecular weight compound (e.g., a pain relieving substance or mixture of pain relieving substances) is transdermally delivered to cells of the body using an embodiment described herein. The delivered agent can be, for example, any one or more of a number of compounds, including non-steroidal anti-inflammatory drugs (NSAIDs) that are frequently administered systemically. These include ibuprofen (2-(isobutylphenyl)-propionic acid); methotrexate (N-[4-(2,4 diamino 6-pteridinyl-methyl]methylamino]benzoyl)-L-glutamic acid); aspirin (acetylsalicylic acid); salicylic acid; diphenhydramine (2-(diphenylmethoxy)-NN-dimethylethylamine hydrochloride); naproxen (2-naphthaleneacetic acid, 6-methoxy-9-methyl-, sodium salt, (−)); phenylbutazone (4-butyl-1,2-diphenyl-3,5-pyrazolidinedione); sulindac-(2)-5-fluoro-2-methyl-1-[[p-(methylsulfinyl)phenyl]methylene-]-1H-indene-3-acetic acid; diflunisal (2',4', -difluoro-4-hydroxy-3-biphenylcarboxylic acid; piroxicam (4-hydroxy-2-methyl-N-2-pyridinyl-2H-1, 2-benzothiazine-2-carboxamide 1,1-dioxide, an oxicam; indomethacin (1-(4-chlorobenzoyl)-5-methoxy-2-methyl-H-indole-3-acetic acid); meclofenamate sodium (N-(2,6-dichloro-m-tolyl) anthranilic acid, sodium salt, monohydrate); ketoprofen (2-(3-benzoylphenyl)-propionic acid; tolmetin sodium (sodium 1-methyl-5-(4-methylbenzoyl-1H-pyrrole-2-acetate dihydrate); diclofenac sodium (2-[(2,6-dichlorophenyl)amino]benzeneatic acid, monosodium salt); hydroxychloroquine sulphate (2-{[4-[(7-chloro-4-quinolyl)amino]pentyl]ethylamino}ethanol sulfate (1:1); penicillamine (3-mercapto-D-valine); flurbiprofen ([1,1-biphenyl]-4-acetic acid, 2-fluoro-alphamethyl-, (+−.)); cetodolac (1-8-diethyl-13,4,9, tetra hydropyrano-[3-4-13]indole-1-acetic acid; mefenamic acid (N-(2,3-xylyl)anthranilic acid; and diphenhydramine hydrochloride (2-diphenyl methoxy-N, N-di-methylethamine hydrochloride).

The transdermal delivery systems described herein, which contain NSAIDs, desirably comprise an amount of the compound that is therapeutically beneficial for the treatment or prevention of disease or inflammation. Several studies have determined an appropriate dose of an NSAID for a given treatment or condition. (See e.g., Woodin, R N, August: 26-33 (1993) and Amadio et al., Postgrduate Medicine, 93(4):73-97 (1993)). The maximum recommended daily dose for several NSAIDs is listed in TABLE 1.

A sufficient amount of NSAID can be incorporated into a transdermal delivery system described herein such that a therapeutically effective amount of NSAID is effectively delivered to a subject. For example, about 0.5 ml of the transdermal delivery system described herein is applied in a single application. A therapeutically effective amount of ibuprofen is about 800 mg/dose. Accordingly, a 30 ml bottle containing a tranderdmal delivery system formulation and ibuprofen can contain 48 grams of ibuprofen such that 800 mg of ibuprofen is provided in each 0.5 ml. Because the transdermal delivery systems described herein can provide a delivered agent in a site-specific manner, a lower total dose of therapeutic agent, as compared to the amounts provided systemically, will provide therapeutic benefit. Additionally, greater therapeutic benefit can be gained by using a transdermal delivery system described herein because a greater concentration of therapeutic agent (e.g., an NSAID) can be provided to the particular site of inflammation. That is, in contrast to systemic administration, which applies the same concentration of therapeutic to all regions of the body, a transdermal delivery system can site-specifically provide the therapeutic agent and, thereby, provide a much greater regional concentration of the agent than if the same amount of therapeutic were administered systemically.

TABLE 1

| Agent | Maximum Recommended Daily Dose |
| --- | --- |
| Indomethacin | 100 mg |
| Ibuprofen | 3200 mg |
| Naproxen | 1250 mg |
| Fenoprofen | 3200 mg |
| Tolmetin | 2000 mg |
| Sulindac | 400 mg |
| Meclofenamate | 400 mg |
| Ketoprofen | 300 mg |
| Proxicam | 10 mg |
| Flurbiprofen | 300 mg |
| Diclofenac | 200 mg |

Additional embodiments include a transdermal delivery system that provides a pain relieving mixture comprising capsaicin (e.g., oleoresin capsicum) or Boswellin or both.

Capsaicin (8-methyl-N-vanillyl-6-nonenamide), the pungent component of paprika and peppers, is a potent analgesic. (See U.S. Pat. No. 5,318,960 to Toppo, U.S. Pat. No. 5,885,597 to Botknecht et al., and U.S. Pat. No. 5,665,378 to Davis et al., all of which are hereby incorporated by reference in their entireties). Capsaicin produces a level of analgesia comparable to morphine, yet it is not antagonized by classical narcotic antagonists such as naloxone. Further, it effectively prevents the development of cutaneous hyperalgesia, but appears to have minimal effects on normal pain responses at moderate doses. At high doses capsaicin also exerts analgesic activity in classical models of deep pain, elevating the pain threshold above the normal value. Capsaicin can be readily obtained by the ethanol extraction of the fruit of *Capsicum frutescens* or *Capsicum annum*. Capsaicin and analogs of capsaicin are available commercially from a variety of suppliers, and can also be prepared synthetically by published methods. Aspects of the invention encompass the use of synthetic and natural capsaicin, capsaicin derivatives, and capsaicin analogs.

A form of capsaicin used in several desirable embodiments is oleoresin capsicum. Oleoresin capsicum contains primarily capsaicin, dihydrocapsaicin, nordihydrocapsaicin, homocapsaicin, and homodihydrocapsaicin. The term "capsaicin" collectively refers to all forms of capsaicin, capsicum, and derivatives or modifications thereof. The pungency of these five compounds, expressed in Scoville units, are provided in TABLE 2.

TABLE 2

| Compound | Pungency × 100,000 SU |
| --- | --- |
| Capsaicin | 160 |
| Dihydrocapsaicin | 160 |
| Nordihydrocapsaicin | 91 |
| Homocapsaicin | 86 |
| Homodihydrocapsaicin | 86 |

The transdermal delivery systems that are formulated to contain capsaicin desirably comprise by weight or volume 0.01% to 1.0% capsaicin or 1.0% to 10% oleoresin capsicum. Preferred amounts of this delivered agent include by weight or volume 0.02% to 0.75% capsaicin or 2.0% to 7.0% oleoresin capsicum. For example, the transdermal delivery systems that contain capsaicin can comprise by weight or volume less than or equal to 0.01%, 0.015%, 0.02%, 0.025%, 0.03%, 0.035%, 0.04%, 0.045%, 0.05%, 0.055%, 0.06%, 0.065%, 0.07%, 0.075%, 0.08%, 0.085%, 0.09%, 0.095%, 0.1%, 0.15%, 0.175%, 0.2%, 0.225%, 0.25%, 0.275%, 0.3%, 0.325%, 0.35%, 0.375%, 0.4%, 0.425%, 0.45%, 0.475%, 0.5%, 0.55%, 0.6%, 0.65%, 0.7%, 0.75%, 0.8%, 0.85%, 0.9%, 0.95%, and 1.0% capsaicin. The transdermal delivery systems of that contain capsaicin can also comprise an amount of capsaicin by weight or volume that is greater than 1.0%, such as 1.2%, 1.5%, 1.8%, 2.0%, 2.2%, 2.5%, 2.8%, 3.0%, 3.5%, 4.0%, 4.5%, and 5.0%. Similarly, the transdermal delivery systems that contain oleoresin capsicum can comprise an amount of oleoresin capsicum less than 1.0%, 1.5%, 2.0%, 2.5%, 3.0%, 3.5%, 4.0%, 4.5%, 5.0%, 5.5%, 6.0%, 6.5%, 7.0%, 7.5%, 7.5%, 8.0%, 8.5%, 9.0%, 9.5%, 10.0%, 11.0%, 12.0%, and 13.0%.

Boswellin, also known as Frankincense, is an herbal extract of a tree of the Boswellia family. Boswellin can be obtained, for example, from *Boswellia thurifera*, *Boswellia carteri*, *Boswellia sacra*, and *Boswellia serrata*. There are many ways to extract Boswellin and Boswellin gum resin and boswellic acids are obtainable from several commercial suppliers (a 65% solution of Boswellic acid is obtainable from Nature's Plus). Some suppliers also provide creams and pills having Boswellin with and without capsaicin and other ingredients. Embodiments of the invention comprise Boswellin and the term "Boswellin" collectively refers to Frankincense, an extract from one or more members of the Boswellia family, Boswellic acid, synthetic Boswellin, or modified or derivatized Boswellin.

The transdermal delivery systems that contain Boswellin desirably comprise 0.1% to 10% Boswellin by weight or volume. Preferred amounts of this delivered agent include 1.0% to 5.0% Boswellin by weight. For example, the transdermal delivery systems that contain Boswellin can comprise by weight or volume less than or equal to 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, and 2.0%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 2.95%, 3.0%, 3.1%, 3.15%, 3.2%, 3.25%, 3.3%, 3.35%, 3.4%, 3.45%, 3.5%, 3.55%, 3.6%, 3.65%, 3.7%, 3.75%, 3.8%, 3.85%, 3.9%, 3.95%, 4.0%, 4.1%, 4.15%, 4.2%, 4.25%, 4.3%, 4.35%, 4.4%, 4.45%, 4.4%, 4.45%, 4.5%, 4.55%, 4.6%. 4.65%, 4.7%, 4.75%, 4.8%, 4.85%, 4.9%, 4.95%, and 5.0% Boswellin. The transdermal delivery systems that contain Boswellin can also comprise amounts of Boswellin by weight that are greater than 5.0%, such as 5.5%, 5.7%, 6.0%, 6.5%%, 6.7%, 7.0%, 7.5%, 7.7%, 8.0%, 8.5%, 8.7%, 9.0%, 9.5%, 9.7%, and 10.0% or greater. Additionally, Boswellin from different sources can be combined to compose the Boswellin component of an embodiment. For example, in one embodiment an extract from *Boswellia thurifera* is combined with an extract from *Boswellia serrata*.

Additional embodiments of the invention comprise a transdermal delivery system that can administer a pain relieving solution comprising two or more members selected from the group consisting of NSAIDs, capsacin, and Boswellin. The transdermal delivery systems that include two or more members selected from the group consisting of NSAIDs, capsacin, and Boswellin desirably comprise an amount of delivered agent that can be included in a delivered agent having an NSAID, capsaicin, or Boswellin by itself. For example, if the delivered agent comprises an NSAID, the amount of NSAID that can be used can be an amount recommended in the literature (See e.g., Woodin, R N, August: 26-33 (1993) and Amadio, et al., *Postgrduate Medicine*, 93(4):73-97 (1993)), or an amount listed in TABLE 1. Similarly, if capsaicin is a component of the delivered agents then the transdermal delivery system can comprise by weight or volume less than or equal to 0.01%, 0.015%, 0.02%, 0.025%, 0.03%, 0.035%, 0.04%, 0.045%, 0.05%, 0.055%, 0.06%, 0.065%, 0.07%, 0.075%, 0.08%, 0.085%, 0.09%, 0.095%, 0.1%, 0.15%, 0.175%, 0.2%, 0.225%, 0.25%, 0.275%, 0.3%, 0.325%, 0.35%, 0.375%, 0.4%, 0.425%, 0.45%, 0.475%, 0.5%, 0.55%, 0.6%, 0.65%, 0.7%, 0.75%, 0.8%, 0.85%, 0.9%, 0.95%, and 1.0% capsaicin or less than 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 11.0%, 12.0%, 13.0%, oleoresin capsicum. Further, if Boswellin is a component of the delivered agents, then the delivery system can comprise by weight or volume less than or equal to 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2.0%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 2.95%, 3.0%, 3.1%, 3.15%, 3.2%, 3.25%, 3.3%, 3.35%, 3.4%, 3.45%, 3.5%, 3.55%, 3.6%, 3.65%, 3.7%, 3.75%, 3.8%, 3.85%, 3.9%, 3.95%, 4.0%, 4.1%, 4.15%, 4.2%, 4.25%, 4.3%, 4.35%, 4.4%, 4.45%, 4.4%, 4.45%, 4.5%, 4.55%, 4.6%, 4.65%, 4.7%, 4.75%, 4.8%, 4.85%, 4.9%, 4.95%, 5.0%, 5.5%, 5.7%, 6.0%, 6.5%%, 6.7%, 7.0%, 7.5%, 7.7%, 8.0%, 8.5%, 8.7%, 9.0%, 9.5%, 9.7%, and 10.0% Boswellin.

In addition to low molecular weight delivered agents, many medium molecular weight delivered agents (eg., humates) can be delivered to cells in the body by using an embodiment of the transdermal delivery system. Synthetic humates ("hepsyls") are medium molecular weight compounds (1,000 to 100,000 daltons), which are known to be strong antiviral and antimicrobial medicaments. (See International Application Publication No. WO 9834629 to Laub, herein expressly incorporated by reference in its entirety). Hepsyls are generally characterized as polymeric phenolic materials comprised of conjugated aromatic systems to which are attached hydroxyl, carboxyl, and other covalently bound functional groups. A transdermal delivery system that can provide hepsyls to cells of the body has several pharmaceutical uses, including but not limited to, treatment of topical bacterial and viral infections.

Accordingly, in another aspect of the invention, a transdermal. delivery system that can provide a medium molecular weight compound (e.g., a form of hepsyl) to cells of the body is provided. As described above, many different medium molecular weight compounds can be provided using an embodiment of a transdermal delivery system described herein and the use of a medium molecular weight hepsyl as a delivered agent is intended to demonstrate that embodiments of the invention can deliver many medium molecular weight compounds to cells of the body.

In some embodiments, amino acids, peptides, nucleotides, nucleosides, and nucleic acids are transdermally delivered to cells in the body using an embodiment of the transdermal delivery system described herein. That is, any amino acid or peptide having at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150, 200, 300, 400, 500, 600, 700, 800, 900, 1000, 1500, 2000, 2500, 3000, 3500, 4000, 4500, 5000, 7000, or 10,000 or more amino acids can be incorporated into a transdermal delivery system described herein and said delivered agent can be delivered to cells in the body shortly after application of the composition. These embodiments can be used, for example, to stimulate an immune response, promote wound healing, induce collagen synthesis, or to supplement collagen.

Similarly, any nucleotide or nucleoside, modified nucleotide or nucleoside, or nucleic acid having at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 75, 100, 125, 150, 200, 300, 400, 500, 600, 700, 800, 900, 1000, 1500, 2000, 2500, 3000, 3500, 4000, 4500, 5000, 7000, or 10,000 or more nucleotides can be incorporated into a transdermal delivery system described herein and said delivered agent can be delivered to cells in the body shortly after application of the composition. These embodiments can also be used, for example, to stimulate an immune response, promote wound healing, or induce collagen synthesis.

In addition to low molecular weight delivered agents and medium molecular weight delivered agents, several high molecular weight delivered agents (e.g., glycoproteins) can be delivered to cells in the body by using an embodiment of the transdermal delivery system. Glycoproteins are high molecular weight compounds, which are generally characterized as conjugated proteins containing one or more heterosaccharides as prosthetic groups. The heterosaccharides are usually branched but have a relatively low number of sugar residues, lack a serially repeating unit, and are covalently bound to a polypeptide chain. Several forms of glycoproteins are found in the body. For example, many membrane bound proteins are glycoproteins, the substances that fill the intercellular spaces (e.g., extracellular matrix proteins) are glycoproteins, and the compounds that compose collagens, proteoglycans, mucopolysaccharides, glycosaminoglycans, and ground substance are glycoproteins. A delivery system that can administer glycoproteins to cells of the body has several pharmaceutical and cosmetic uses, including but not limited to, the restoration of skin elasticity and firmness (e.g., the reduction in the appearance of fine lines and wrinkles by transdermal delivery of collagen) and the restoration of flexible and strong joints (e.g., water retention in joints can be increased by transdermal delivery of proteoglycans).

Accordingly, in another aspect of the invention, a transdermal delivery system that can administer a high molecular weight compound (e.g., a form of collagen or fragment thereof) to cells of the body is provided. As described above, many different high molecular weight compounds can be administered by using an embodiment of a transdermal delivery system of the invention and the use of a high molecular weight collagen as a delivered agent is intended to demonstrate that embodiments of the invention can deliver many high molecular weight compounds to cells of the body.

Collagens exist in many forms and can be isolated from a number of sources. Additionally, several forms of collagen can be obtained commercially (e.g., Brooks Industries Inc., New Jersey). Many low molecular weight collagens can be made, for example, by hydrolysis. Several transdermal delivery systems of the invention can deliver collagens having molecular weights below 6,000 daltons. Additionally, several high molecular weight collagens exist. Some are isolated from animal or plant sources and some are synthesized or produced through techniques common in molecular biology. Several transdermal delivery systems of the invention can deliver collagens having molecular weights of 1,000 daltons to greater than 2,000,000 daltons. That is, embodiments of the transdermal delivery systems can deliver collagens having molecular weights of less than or equal to or greater than 1,000, 1,500, 2,000, 2,500, 3,000, 3,500, 4,000, 4,500, 5,000, 5,500, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 46,000, 47,000, 48,000, 49,000, 50,000, 51,000, 52,000, 53,000, 54,000, 55,000, 56,000, 57,000, 58,000, 59,000, 60,000, 61,000, 62,000, 63,000, 64,000, 65,000, 66,000, 67,000, 68,000, 69,000, 70,000, 75,000, 80,000, 85,000, 90,000, 95,000, 100,000, 125,000, 150,000, 175,000, 200,000, 225,000, 250,000, 275,000, 300,000, 350,000, 400,000, 450,000, 500,000, 600,000, 700,000, 800,000, 900,000, 1,000,000, 1,500,000, 1,750,000, and 2,000,000 daltons.

In some embodiments, the commercially available collagen "Hydrocoll EN-55" was provided as the delivered agent and was delivered to cells of a test subject. This form of collagen is hydrolyzed collagen and has a molecular weight of 2,000 daltons. In another embodiment, the commercially available "Ichtyocollagene" or marine collagen (Sederma or Croda of Parsippany, N.J.) was provided as the delivered agent and was delivered to a test subject. This form of soluble collagen has a molecular weight of greater than 100,000 daltons. In another embodiment, the commercially available collagen "Solu-Coll" was provided as the delivered agent and was delivered to cells of a test subject. This form of collagen is a soluble collagen having a molecular weight of 300,000 daltons. An additional embodiment includes the commercially available collagen "Plantsol", which is obtained from yeast and has a molecular weight of 500,000 daltons. This collagen was also provided as a delivered agent and was delivered to cells of a test subject.

The transdermal delivery systems that contain a form of collagen or fragment thereof desirably comprise by weight or volume between 0.1% to 85.0% of the delivered agent depending on the type and form of the collagen, its solubility, and the intended application. That is, some transdermal delivery systems comprise by weight or volume less than or equal to or greater than 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0% 8.25%, 8.5%, 8.75%, 9.0%, 9.25%, 9.5%, 9.75%, 10.0%, 10.25%, 10.5%, 10.75%, 11.0%, 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 41.0%, 42.0%, 43.0%, 44.0%, 45.0%, 46.0%, 47.0%, 48.0%, 49.0%, 50.0%, 51%, 52%, 53%, 54%, 55%, 56%, 57%, 58%, 59%, 69%, 70%, 71%, 72%, 73%, 74%, 75%, 76%, 77%, 78%, 79%, 80%, 81%, 82%, 83%, 84%, or 85% collagen or fragment thereof.

For example, embodiments having Hydrocoll-EN55 can comprise by weight or volume less than or equal to or greater than 1.0%, 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, 10.0%, 10.25%, 10.5%, 10.75%, 11.0%, 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 41.0%, 42.0%, 43.0%, 44.0%, 45.0%, 46.0%, 47.0%, 48.0%, 49.0%, 50.0%, 51%, 52%, 53%, 54%, 55%, 56%, 57%, 58%, 59%, 69%, 70%, 71%, 72%, 73%, 74%, 75%, 76%, 77%, 78%, 79%, 80%, 81%, 82%, 83%, 84%, or 85% Hydrocoll-EN-55.

Embodiments having marine collagen can comprise by weight or volume less than or equal to or greater than 1.0%, 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0% 8.25%, 8.5%, 8.75%, 9.0%, 9.25%, 9.5%, 9.75%, 10.0%, 10.25%, 10.5%, 10.75%, 11.0%, 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 41.0%, 42.0%, 43.0%, 44.0%, 45.0%, 46.0%, 47.0%, 48.0%, 49.0%, 50.0%, 51%, 52%, 53%, 54%, 55%, 56%, 57%, 58%, 59%, 69%, 70%, 71%, 72%, 73%, 74%, 75%, 76%, 77%, 78%, 79%, 80%, 81%, 82%, 83%, 84%, or 85% marine collagen.

Further, transdermal delivery systems that contain Solu-Coll can comprise by weight or volume less than or equal to or greater than 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, or 2.0% Solu-Coll.

Additionally, transdermal delivery systems that contain Plantsol can comprise by weight or volume less than or equal to or greater than 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2.0%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 2.95%, 3.0%, 3.1%, 3.15%, 3.2%, 3.25%, 3.3%, 3.35%, 3.4%, 3.45%, 3.5%, 3.55%, 3.6%, 3.65%, 3.7%, 3.75%, 3.8%, 3.85%, 3.9%, 3.95%, or 4.0%, Plantsol.

In other embodiments of the invention, a transdermal delivery system that can provide a collagen solution comprising two or more forms of collagen (e.g., Hydro-Coll EN-55, marine collagen, Solu-coll, or Plantsol) is provided. The transdermal delivery systems that include two or more forms of collagen desirably comprise an amount of delivered agent that can be included in a delivered agent having the specific type of collagen by itself. For example, if the mixture of delivered agents comprises Hydro-Coll EN55, the amount of Hydro-Coll EN55 in the transdermal delivery system can comprise by weight or volume less than or equal to or greater than 1.0%, 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0% 8.25%, 8.5%, 8.75%, 9.0%, 9.25%, 9.5%, 9.75%, 10.0%, 10.25%, 10.5%, 10.75%, 11.0%, 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 41.0%, 42.0%, 43.0%, 44.0%, 45.0%, 46.0%, 47.0%, 48.0%, 49.0%, 50.0%, 51%, 52%, 53%, 54%, 55%, 56%, 57%, 58%, 59%, 69%, 70%, 71%, 72%, 73%, 74%, 75%, 76%, 77%, 78%, 79%, 80%, 81%, 82%, 83%, 84%, or 85% Hydrocoll-EN-55.

If the mixture of delivered agents has marine collagen, then the amount of marine collagen in the delivery system can comprise by weight or volume less than or equal to or greater than 1.0%, 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0% 8.25%, 8.5%, 8.75%, 9.0%, 9.25%, 9.5%, 9.75%, 10.0%, 10.25%, 10.5%, 10.75%, 11.0%, 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 41.0%, 42.0%, 43.0%, 44.0%, 45.0%, 46.0%, 47.0%, 48.0%, 49.0%, 50.0%, 51%, 52%, 53%, 54%, 55%, 56%, 57%, 58%, 59%, 69%, 70%, 71%, 72%, 73%, 74%, 75%, 76%, 77%, 78%, 79%, 80%, 81%, 82%, 83%, 84%, or 85% marine collagen.

Similarly if the mixture of delivered agents has Solu-coll, then the amount of Solu-coll in the delivery system can comprise by weight or volume less than or equal to or greater than 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, or 2.0% or Solu-Coll. Further, if the mixture of delivered agents has Plantsol, then the amount of Plantsol in the delivery system can comprise by weight or volume less than or equal to or greater than 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2.0%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 2.95%, 3.0%, 3.1%, 3.15%, 3.2%, 3.25%, 3.3%, 3.35%, 3.4%, 3.45%, 3.5%, 3.55%, 3.6%, 3.65%, 3.7%, 3.75%, 3.8%, 3.85%, 3.9%, 3.95%, or 4.0% Plantsol.

Additionally, modified or stabilized collagens or collagen derivatives are contemplated for use in some of the embodiments described herein. Particularly preferred are collagens that are resistant to proteases. Recombinant engineering can be used to generate collagens or fragments thereof that lack protease cleavage sites for example. Resistant collagens or fragments thereof can also be prepared by incorporating D-amino acids in synthetically prepared collagens or fragments thereof. Cross-linked collagens can also be used. (See e.g., Charulatha, *Biomaterials* February; 24(5):759-67 (2003), herein expressly incorporated by reference in its entirety). Still further, amidated collagen or collagen fragments can be prepared using synthetic chemistry and these collagen derivatives can be mixed with an ethoxylated oil with or without water or alcohol so as to form a transdermal delivery system containing collagen. Several techniques to create synthetic, recombinant, or cross-linked collagens are known to those of skill in the art and many are commercially available.

Still further, protease resistant fragments of collagen can be prepared and isolated using conventional techniques. By one approach, marine collagen, procollagen, or collagen obtained from human placenta is incubated with bovine serum, pepsin, or bacterial collagenase for one hour and the preparation is then separated by gel electrophoresis, size exclusion, reverse phase, or ionic exchange chromatography (e.g., FPLC or HPLC). Protease resistant fragments of collagen (e.g., 15 kDa or 30 kDa; see e.g., Tasab et al., *JBC* 277(38):35007 (2002) or 38 kDa see e.g., Odermatt et al., *Biochem J.* May 1; 211(2):295-302 (1983) both of which are herein expressly incorporated by reference in their entireties) are separated from the hydrolytic products and these fragments are isolated from the column and concentrated (e.g., centricon filters) or lyophilized using conventional techniques. The protease resistant fragments of collagen are then incorporated into a transdermal delivery system, as described herein. Alternatively, the protease resistant domain of collagen can be prepared synthetically or obtained commercially (e.g., pepsinized collagens can also be obtained from Chemicon of Temecula, Calif.).

An additional delivered agent that can be included in a transdermal delivery system is Etioline (Sederma or Croda of Parsippany, N.J.). Etioline is a tyrosinase inhibitor made from the extract *Mitracarpe* and bearberry that effectively whitens the skin. Formulations of a transdermal delivery system described herein containing Etioline (e.g., at 1%, 2%, 3%, 4%, 5%, 6%, 7%, 8%, 9%, 10%, 11%, 12%, 13%, 14%, 15%, 16%, 17%, 18%, 19%, or 20%) are also embodiments of the invention. Another skin brightening or whitening formulation of a transdermal delivery system comprises Melaslow (Sederma of Parsippany, N.J.). Melaslow is an extract made from *Citrus reticulate Blanco* var. Unshiu. Melaslow is also an inhibitor of melanogenesis and formulations of a transdermal delivery system described herein containing Melaslow (e.g., at 1%, 2%, 3%, 4%, 5%, 6%, 7%, 8%, 9%, 10%, 11%, 12%, 13%, 14%, 15%, 16%, 17%, 18%, 19%, or 20%) are also embodiments of the invention. An additional delivered agent that can be included in a transdermal delivery system is Matrixyl (Sederma or Croda of Parsippany, N.J.). Matrixyl is a compound comprising the peptide KTTKS (SEQ. ID. No. 2), which has been shown to stimulate collagen synthesis. See Katayama et al., J. Biol. Chem. 268, 9941 (1993). Formulations of a transdermal delivery system described herein containing Matrixyl or the peptide KTTKS (SEQ. ID. No. 2) (e.g., at 1%, 2%, 3%, 4%, 5%, 6%, 7%, 8%, 9%, 10%, 11%, 12%, 13%, 14%, 15%, 16%, 17%, 18%, 19%, or 20%) are also embodiments of the invention. The section below describes the manufacture and use of several penetration enhancers that enable the delivery of both low and high molecular weight molecules to cells of the body.

Penetration Enhancers

A penetration enhancer included in many embodiments of the invention is comprised of two components—a hydrophobic component and a hydrophilic component. Desirably, the hydrophobic component comprises a polyether compound, such as an ethoxylated vegetable, nut, synthetic, or animal oil, which has the ability to reduce the surface tension of materials that are dissolved into it. Not wanting to be tied to any particular mechanism or mode of action and offered only to expand the knowledge in the field, it is contemplated that the attachment of poly (ethylene oxide) to the components of a particular oil occurs not on a particular functional group but rather the polyethylene oxide chains begin to grow from unsaturated C=C bonds and from the occasional glycerol unit. Because an ethoxylated oil, such as ethoxylated macadamia nut oil, is a mixture of various fatty acids, fatty alcohols, and fatty amines, the components of the oil may have varying amounts of ethoxylation. Accordingly, measurements of ethoxylation/molecule (e.g., 16 ethoxylations/molecule) are an average of the amount of ethoxylation present on the components of the oil rather than on any specific component itself.

Preferred ethoxylated oils can be obtained or created from, for example, macadamia nut oil, meadowfoam, castor oil, jojoba oil, corn oil, sunflower oil, sesame oil, and emu oil. Many of these oils are commercially available from Floratech of Gilbert, Ariz. or other suppliers. Alternatively, ethoxylated oils can be prepared by reacting the oil with ethylene oxide. Pure carrier oils that are suitable for ethoxylation so as to create a penetration enhancer for use with the transdermal delivery systems described herein are included in TABLES 3-17 and can be obtained from Esoteric oils Pty. Ltd., Pretoria South Africa. TABLES 3-17 also list the component fatty acids of these oils, all of which are individually suitable for ethoxylation and incorporation into an embodiment of a transdermal delivery system. That is, it is contemplated that ethoxylated fatty acids, ethoxylated fatty alcohols, and ethoxylated fatty amines, in particular ethoxylated fatty acids, ethoxylated fatty alcohols, and ethoxylated fatty amines that contain 12, 13, 14, 15, 16, 17, 18, or 19 ethoxylations are suitable penetration enhancers for use in the transdermal delivery systems described herein. These ethoxylated oil components can be used individually as penetration enhancers or as supplements to other penetration enhancers (e.g., ethoxylated macadamia nut oil).

TABLE 3

Macadamia nut oil

| Fatty acids | | Range |
|---|---|---|
| Myristic | C14 | 0.6-1.6% |
| Palmitic | C16 | 7.0-11.0% |
| Palmitoleic | C16:1 | 18.0-25.0% |
| Stearic | C18 | 2.0-4.0% |
| Oleic | C18:1 | 55.0-62.0% |
| Linoleic | C18:2 | 1.0-4.0% |
| Arachidic | C20 | 2.0-4.0% |
| Eicosenoic | C20:1 | 2.0-4.0% |

TABLE 4

Apricot kernel oil

| Fatty acids | | Range | Typical |
|---|---|---|---|
| Palmitic | C16:0 | 3.0-6.0% | 4.28% |
| Palmitoleic | C16:1 | trace-1.4% | 0.70% |
| Stearic | C18:0 | trace-2.0% | 1.12% |
| Oleic | C18:1 | 55.0-70.0% | 69.62% |
| Linoleic | C18:2 | 20.0-35.0% | 23.34% |
| Linolenic | C18:3 | trace-1.0% | 0.22% |
| Eicosenoic | C20:1 | trace-1.0% | 0.18% |

TABLE 5

Avocado oil

| Fatty acids | | Range | Typical |
|---|---|---|---|
| Palmitic | C16:0 | 12.0-20.0% | 14.25% |
| Palmitoleic | C16:1 | 2.0-10.0% | 5.84% |
| Stearic | C18:0 | 0.1-2.0% | 0.1% |
| Oleic | C18:1 | 55.0-75.0% | 65.4% |
| Linoleic | C18:2 | 9.0-17.0% | 14.74% |
| Linolenic | C18:3 | 0.1-2.0% | 0.8% |

TABLE 6

Evening Primrose oil

| Fatty acids | | Range | Typical |
|---|---|---|---|
| Palmitic | C16:0 | 5.5-7.0% | 5.9% |
| Stearic | C18:0 | 1.5-2.5% | 1.7% |
| Oleic | C18:1 | 5.0-11.0% | 5.8% |
| Linoleic | C18:2 | 70.0-77.0% | 75.1% |
| Gamma Linolenic | C18:3 | 9.0-10.9% | 10.6% |
| Alpha Linolenic | C18:3 | 1.0% max | 0.4% |
| Icosanoic | C20:0 | 1.0% max | 0.2% |
| Icosenoic | C20:1 | 1.0% max | .01% |

TABLE 7

Grape seed oil

| Fatty acids | | Range | Typical |
|---|---|---|---|
| Palmitic | C16:0 | 6.0-9.0% | 6.5% |
| Palmitoleic | C16:1 | less 1% | 0.2% |
| Stearic | C18:0 | 3.0-6.0% | 3.7% |
| Oleic | C18:1 | 12.0-25.0% | 23.4% |
| Linoleic | C18:2 | 60.0-75.0% | 65.3% |
| Alpha Linolenic | C18:3 | less than 1.5% | 0.2% |
| Icosanoic | C20:0 | less than 0.5% | 0.2% |
| Icosenoic | C20:1 | less than 0.5% | 0.2% |
| Docosanoic | C22:0 | less than 0.3% | 0.2% |

TABLE 8

Hazelnut oil

| Fatty acids | | Range |
|---|---|---|
| Palmitic | C16:0 | 4.0-8.0% |
| Palmitoleic | C16:1 | 0.1-0.6% |
| Stearic | C18:0 | 1.5-3.5% |
| Oleic | C18:1 | 68.0-85.0% |
| Linoleic | C18:2 | 7.0-15.0% |
| Linolenic | C18:3 | 0.1-0.5% |
| Arachidic | C20:0 | 0.1-0.5% |
| Gadoleic | C20:1 | 0.1-0.3% |
| Behenic | C22:0 | 3.0% MAX |

TABLE 9

Jojoba oil

| Fatty acids | | Range |
|---|---|---|
| Palmitic | C16:0 | 3.0% max |
| Palmitoleic | C16:1 | 1.0% max |
| Stearic | C18:0 | 1.0% max |

TABLE 9-continued

Jojoba oil

| Fatty acids | | Range |
|---|---|---|
| Oleic | C18:1 | 5.0-15.0% |
| Linoleic | C18:2 | 5.0% max |
| Linolenic | C18:3 | 1.0% max |
| Arachidic | C20:0 | 0.5% max |
| Eicosenoic | C20:1 | 65.0-80.0% max |
| Behenic | C22:0 | 0.5% max |
| Erucic | C22:1 | 10.0-20.0% max |
| Lignoceric | C24:0 | 5.0% max |

TABLE 10

Olive oil

| Fatty acids | | Range |
|---|---|---|
| Palmitic | C16:0 | 5.0-12.0% |
| Palmitoleic | C16:1 | 1.0% max |
| Stearic | C18:0 | 3.5% max |
| Oleic | C18:1 | 65.0-80.0% |
| Linoleic | C18:2 | 6.0-25.0% |
| Linolenic | C18:3 | 1.0% max |
| Arachidic | C20:0 | 0.6% max |
| Gadoleic | C20:1 | 0.5% max |
| Behenic | C22:0 | 0.3% max |
| Erucic | C22:1 | 0.2% max |

TABLE 11

Pumpkin seed oil

| Fatty acids | | Range |
|---|---|---|
| Palmitic | C16:0 | 6.0-21.0% |
| Stearic | C18:0 | 3.0-8.0% |
| Oleic | C18:1 | 24.0-41.0% |
| Linoleic | C18:2 | 42.0-60.0% |
| Linolenic | C18:3 | 2.0% max |
| Others | | 2.0% max |

TABLE 12

Rose hip oil

| Fatty acids | | Range |
|---|---|---|
| Mirystic | C14:0 | 0.0-0.3% |
| Palmitic | C16:0 | 3.4-4.4% |
| Palmitoleic | C16:1 | 0.1-0.18% |
| Stearic | C18:0 | 1.5-2.5% |
| Oleic | C18:1 | 14.0-16.0% |
| Linoleic | C18:2 | 43.0-46.0% |
| Linolenic | C18:3 | 31.0-34.0% |
| Arachidic | C20:0 | 0.1-0.9% |
| Gadoleic | C20:1 | 0.0-0.5% |
| Eicosenoic | C20:2 | 0.0-0.5% |
| Behenic | C22:0 | 0.1-0.4% |

TABLE 13

Safflower oil

| Fatty acids | | Range |
|---|---|---|
| Palmitic | C16:0 | 4.0-9.0% |
| Palmitoleic | C16:1 | Trace |
| Stearic | C18:0 | trace-2.5% |

TABLE 13-continued

Safflower oil

| Fatty acids | | Range |
|---|---|---|
| Oleic | C18:1 | 72.0-80.0% |
| Linoleic | C18:2 | 12.0-16.0% |
| Linolenic | C18:3 | trace-0.5% |

TABLE 14

Sesame oil

| Fatty acids | | Range |
|---|---|---|
| Palmitic | C16:0 | 7.0-12.0% |
| Palmitoleic | C16:1 | trace-0.5% |
| Stearic | C18:0 | 3.5-6.0% |
| Oleic | C18:1 | 35.0-50.0% |
| Linoleic | C18:2 | 35.0-50.0% |
| Linolenic | C18:3 | trace-1.0% |
| Eicosenoic | C20:1 | trace-1.0% |

TABLE 15

Sunflower oil

| Fatty acids | | Range |
|---|---|---|
| Palmitic | C16:0 | 5.8% |
| Palmitoleic | C16:1 | 0.1% |
| Stearic | C18:0 | 3.9% |
| Oleic | C18:1 | 15.9% |
| Linoleic | C18:2 | 71.7% |
| Alpha Linolenic | C18:3 | 0.6% |
| Gamma Linolenic | C18:3 | 0.1% |
| Arachidic | C20:0 | 0.3% |
| Gadoleic | C20:1 | 0.2% |
| Tetracosanoic | C24:0 | 0.5% |
| Behenic | C22:0 | 0.7% |

TABLE 16

Walnut oil

| Fatty acids | | Range | Typical |
|---|---|---|---|
| Palmitic | C16:0 | 5.0-8.0% | 6.0% |
| Palmitoleic | C16:1 | less than 1.0% | 0.1% |
| Stearic | C18:0 | 3.0-7.0% | 4.0% |
| Oleic | C18:1 | 25.0-35.0% | 29.8% |
| Linoleic | C18:2 | 45.0-60.0% | 58.5% |
| Alpha Linolenic | C18:3 | less than 0.8% | 0.4% |
| Arachidic | C20:0 | less than 0.5% | 0.3% |
| Eicosenoic | C20:1 | less than 0.5% | 0.2% |

TABLE 17

Wheat germ oil

| Fatty acids | | Range | Typical |
|---|---|---|---|
| Palmitic | C16:0 | 11.0-16.0% | 12.5% |
| Palmitoleic | C16:1 | 1.0% max | 0.2% |
| Stearic | C18:0 | 2.0-6.0% | 2.5% |
| Oleic | C18:1 | 12.0-39.0% | 27.3% |
| Linoleic | C18:2 | 30.0-57.0% | 53.7% |
| Linolenic | C18:3 | 2.0-10.0% | 3.0% |
| Arachidic | C20:0 | 1.0% max | 0.4% |

TABLE 17-continued

Wheat germ oil

| Fatty acids | | Range | Typical |
|---|---|---|---|
| Gadoleic | C20:1 | 0.5% max | 0.2% |
| Behenic | C22:0 | 1.0% max | 0.1% |

In some embodiments, an ethoxylated oil comprises a molar ratio of ethylene oxide:oil of 35:1. A 99% pure ethylene oxide/castor oil having such characteristics can be obtained commercially (BASF) or such an ethoxylated compound can be synthesized using conventional techniques. In other embodiments, the ethoxylated oil is itself the penetration enhancer. That is, it has been discovered that oils that have been ethoxylated 10, 11, 12, 13, 14, 15, 16, 17, 18, or 19 ethoxylations/molecule are sufficiently hydrophobic and sufficiently hydrophilic to allow for transdermal delivery of a variety of delivered agents without water, alcohol, or an aqueous adjuvant. Although the ethoxylated oil can comprise at least 20-25 ethoxylations per molecule or more, preferably, the ethoxylated lipid comprises less than 20 ethoxylations per molecule, e.g., 19, 18, 17, 16, 15, 14, 13, 12, 11, or 10 ethoxylations per molecule.

By using a light, ethoxylated oil (e.g., macadamia nut oil containing approximately 16 ethoxylations/molecule) efficient transdermal delivery of high molecular weight collagen was observed in the absence of *Aloe Vera* and alcohol. Formulations of a transdermal delivery system that contain *Aloe Vera* and an oil with 20-30 ethoxylations/molecule are not as effective as formulations of a transdermal delivery system that contain an oil with 10-19 ethoxylations/molecule (e.g., 16 ethoxylations/molecule) but lacking *Aloe Vera* and alcohol. A greater reduction of fine lines and wrinkles was observed with a transdermal delivery system composed of macadamia nut oil (16 ethoxylations/molecule) and water as compared with a transdermal delivery system composed of castor oil (25 ethoxylations/molecule), water, alcohol, and *Aloe Vera*, for example.

Unexpectedly, it was discovered that a reduction in the number of ethoxylations on a light oil produced a superior transdermal delivery product. This was unexpected because as the amount of ethoxylations on a molecule of oil decreases its miscibility with the aqueous components of the delivery system decreases. Surprisingly, formulations containing 10-19 ethoxylations/molecule were not only miscible but provided very efficient transdermal delivery in the absence of *Aloe Vera*.

Desirable compounds often found in ethoxylated oils that are beneficial for some embodiments and methods described herein are glycerol-polyethylene glycol ricinoleate, the fatty esters of polyethylene glycol, polyethylene glycol, and ethoxylated glycerol. Some of these desirable compounds exhibit hydrophilic properties and the hydrophilic-lipophilic balance (HLB) is preferably maintained between 10 and 18. Any number of methods have been devised to characterize HLB, but perhaps the most widely used is the octanol/water coefficient. (See Calculating log Poct from Structures", by Albert J. Leo, Chemical Reviews, vol 93, pp 1281).

Accordingly, some of the components of the oils in the table above and related fatty acids, fatty alcohols, and fatty amines can be ethoxylated and used as a penetration enhancer or to enhance another penetration enhancer (e.g., ethoxylated macadamia nut oil). For example, some embodiments comprise a penetration enhancer that consists of, consists essentially of, or comprises ethoxylated palmitoleic acid, ethoxylated oleic acid, ethoxylated gondoic acid, or ethoxylated erucic acid. These compounds can be prepared synthetically or isolated or purified from oils that contain large quantities of these fatty acids and the synthesized, isolated, or purified fatty acids can then be reacted with ethylene oxide.

That is, a transdermal delivery system of the invention can comprise a penetration enhancer that contains, for example, ethoxylated palmitoleic acid, ethoxylated oleic acid, ethoxylated gondoic acid, or ethoxylated erucic acid, wherein the amount of one or more of the fatty acids is at least, more than, or an amount equal to 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, 10.0%, 10.25%, 10.5%, 10.75%, 11.0%, 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.25%, 40.5%, 40.75%, 41.0%, 41.25%, 41.5%, 41.75%, 42.0%, 42.25%, 42.5%, 42.75%, 43.0%, 43.25%, 43.5%, 43.75%, 44.0%, 44.25%, 44.5%, 44.75%, 45.0%, 45.25%, 45.5%, 45.75%, 46.0%, 46.25%, 46.5%, 46.75%, 47.0% 47.25%, 47.5%, 47.75%, 48.0%, 48.25%, 48.5%, 48.75%, 49.0%, 49.25%, 49.5%, 49.75%, 50.0%, 50.25%, 50.5%, 50.75%, 51.0%, 51.25%, 51.5%, 51.75%, 52.0%, 52.25%, 52.5%, 52.75%, 53.0%, 53.25%, 53.5%, 53.75%, 54.0%, 54.5%, 54.0%, 54.5%, 55.0%, 55.5%, 56.0%, 56.5%, 57.0%, 57.5%, 58.0%, 58.5%, 59.0%, 59.5%, 60.0%, 60.5%, 61.0%, 61.5%, 62.0%, 62.5%, 63.0%, 63.5%, 64.0%, 64.5%, 65.0%, 65.5%, 66.0%, 66.5%, 67.0%, 67.5%, 68.0%, 68.5%, 69.0%, 69.5%, 70.0%, 70.5%, 71.0%, 71.5%, 72.0%, 72.5%, 73.0%, 73.5%, 74.0%, 74.5%, 75.0%, 75.5%, 76.0%, 76.5%, 77.0%, 77.5%, 78.0%, 78.5%, 79.0%, 79.5%, 80.0%, 80.5%, 81%, 81.5%, 82%, 82.5%, 83%, 83.5%, 84%, 84.5%, 85%. 85.5%, 86%, 86.5%, 87%, 87.5%, 88%, 88.5%, 89%, 89.5%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, or 100% of the total fatty acid content in the composition. In some embodiments, more than one ethoxylated compound is added or another hydrophobic compound is added (e.g., Y-Ling-Y-Lang oil; Young Living Essential Oils, Lehl, Utah)) to balance or enhance the penetration enhancer. Preferred embodiments include ethoxylated macadamia nut oil that has been supplemented with ethoxylated palmitoleic acid, ethoxylated oleic acid, ethoxylated gondoic acid, or ethoxylated erucic acid.

Depending on the type of delivered agent and the intended application, the amount of ethoxylated lipid(s) in the delivery system can vary. For example, delivery systems of the invention can comprise between 0.1% and 99% by weight or volume ethoxylated compound(s). That is, embodiments of the invention can comprise by weight or volume less than or equal to or greater than 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0% 8.25%, 8.5%, 8.75%, 9.0%, 9.25%, 9.5%, 9.75%, 10.0%, 10.25%, 10.5%, 10.75%, 11.0%, 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, ethoxylated lipid(s), preferably an ethoxylated oil or fatty acid or combination of fatty acids.

The hydrophilic component of the penetration enhancer can comprise an alcohol, a non-ionic solubilizer, or an emulsifier. Compounds such as ethylene glycol, propylene glycol, dimethyl sulfoxide (DMSO), dimethyl polysiloxane (DMPX), oleic acid, caprylic acid, isopropyl alcohol, 1-octanol, ethanol (denatured or anhydrous), and other pharmaceutical grade or absolute alcohols with the exception of methanol can be used. Preferred embodiments comprise an alcohol (e.g., absolute isopropyl alcohol), which is commercially available. As above, the amount of hydrophilic component in the penetration enhancer depends on the type of the delivered agent and the intended application. The hydrophilic component of a penetration enhancer of the invention can comprise between 0.1% and 50% by weight or volume. That is, a delivery system of the invention can comprise by weight or volume less than or equal to or greater than 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0% 8.25%, 8.5%, 8.75%, 9.0%, 9.25%, 9.5%, 9.75%, 10.0%, 10.25%, 10.5%, 10.75%, 11.0%, 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 41.0%, 42.0%, 43.0%, 44.0%, 45.0%, 46.0%, 47.0%, 48.0%, 49.0%, or 50.0% hydrophilic component.

In addition to a delivered agent and penetration enhancer, the transdermal delivery systems described herein can comprise an aqueous adjuvant. The section below describes the incorporation of aqueous adjuvants in formulations of transdermal delivery systems, in particular, *Aloe Vera*, which can enhance the delivery of both low and high molecular weight molecules to the skin cells of the body.

Aqueous Adjuvants

Several embodiments of the transdermal delivery system described herein comprise an aqueous adjuvant such as *Aloe Vera* juice or water or both. The term "*Aloe*" refers to the genus of South African plants of the Liliaceae family, of which the *Aloe barbadensis* plant is a species. *Aloe* is an intricate plant, which contains many biologically active substances. (Cohen, et al. in Wound Healing/Biochemical and Clinical Aspects, 1st ed. W B Saunders, Philadelphia (1992)). Over 300 species of *Aloe* are known, most of which are indigenous to Africa. Studies have shown that the biologically active substances are located in three separate sections of the *Aloe* leaf—a clear gel fillet located in the center of the leaf, in the leaf rind or cortex of the leaf and in a yellow fluid contained in the pericyclic cells of the vascular bundles, located between the leaf rind and the internal gel fillet, referred to as the latex. Historically, *Aloe* products have been used in dermatological applications for the treatment of burns, sores and other wounds. These uses have stimulated a great deal of research in identifying compounds from *Aloe* plants that have clinical activity, especially anti-inflammatory activity. (See e.g., Grindlay and Reynolds (1986) J. of Ethnopharmacology 16:117-151; Hart, et al. (1988) J. of Ethnopharmacology 23:61-71). As a result of these studies there have been numerous reports of *Aloe* compounds having diverse biological activities, including anti-tumor activity, anti-gastric ulcer, anti-diabetic, anti-tyrosinase activity, (See e.g., Yagi, et al. (1977) Z. Naturforsch. 32c:731-734), and antioxidant activity (International Application Serial No. PCT/US95/07404).

Recent research has also shown that *Aloe Vera*, a term used to describe the extract obtained from processing the entire leaf, isolated from the *Aloe Vera* species of *Aloe*, can be used as a vehicle for delivering hydrocortisone, estradiol, and testosterone propionate. (See Davis, et al, *JAPMA* 81:1 (1991) and U.S. Pat. No. 5,708,038 to Davis)). As set forth in Davis (U.S. Pat. No. 5,708,308), one embodiment of "*Aloe Vera*" can be prepared by "whole-leaf processing" of the whole leaf of the *Aloe barbadensis* plant. Briefly, whole leaves obtained from the *Aloe barbadensis* plant are ground, filtered, treated with cellulase (optional) and activated carbon and lyophilized. The lyophilized powder is then reconstituted with water prior to use.

*Aloe Vera* can be obtained commercially through Aloe Laboratories, for example. In other embodiments, the *Aloe Vera* is made as follows. First, the leaves are manually harvested. Next, the leaves are washed with water and the thorns on both ends are cut. The leaves are then hand-filleted so as to extract the inner part of the leaf. The inner gel is passed through a grinder and separator to remove fiber from the gel. Then the gel is put into a pasteurizing tank where L-Ascorbic Acid (Vitamin C) and preservatives are added. The gel is pasteurized at 85° C. for 30 minutes. After pasteurization, the gel is put into a holding tank for about one or two days, after which the gel is sent through a ½ micron filter. Finally, the gel is cooled down through a heat exchanger and stored in a steamed, sanitized and clean 55 gallon drum. The above described sources and manufacturing methods of *Aloe Vera* are given as examples and not intended to limit the scope of the invention. One of ordinary skill in the art will recognize that *Aloe Vera* is a well known term of art, and that *Aloe Vera* is available from various sources and manufactured according to various methods.

Absolute *Aloe Vera* (100% pure) can also be obtained from commercial suppliers (Lily of the Desert, Irving, Tex.). *Aloe Vera* juice, prepared from gel fillet, has an approximate molecular weight of 200,000 to 1,400,000 daltons. Whole leaf *Aloe Vera* gel has a molecular weight of 200,000 to 3,000,000 depending on the purity of the preparation. Although, preferably, the embodiments of the invention having *Aloe Vera* comprise *Aloe Vera* juice, other extracts from a member of the Liliaceae family can be used (e.g., an extract from another *Aloe* species).

Transdermal delivery systems having *Aloe Vera* can comprise between 0.1% to 85.0% by weight or volume *Aloe Vera*. That is, embodiments of the invention can comprise by weight or volume less than or equal to or greater than 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0% 8.25%, 8.5%, 8.75%, 9.0%, 9.25%, 9.5%, 9.75%, 10.0%, 10.25%, 10.5%, 10.75%, 11.0%, 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.25%, 40.5%, 40.75%, 41.0%, 41.25%, 41.5%, 41.75%, 42.0%, 42.25%, 42.5%, 42.75%, 43.0%, 43.25%, 43.5%, 43.75%, 44.0%, 44.25%, 44.5%, 44.75%, 45.0%, 45.25%, 45.5%, 45.75%, 46.0%, 46.25%, 46.5%, 46.75%, 47.0% 47.25%, 47.5%, 47.75%, 48.0%, 48.25%, 48.5%, 48.75%, 49.0%, 49.25%, 49.5%, 49.75%, 50.0%, 50.25%, 50.5%, 50.75%, 51.0%, 51.25%, 51.5%, 51.75%, 52.0%, 52.25%, 52.5%, 52.75%, 53.0%, 53.25%, 53.5%, 53.75%, 54.0%, 54.5%, 54.0%, 54.5%, 55.0%, 55.5%, 56.0%, 56.5%, 57.0%, 57.5%, 58.0%, 58.5%, 59.0%, 59.5%, 60.0%, 60.5%, 61.0%, 61.5%, 62.0%, 62.5%, 63.0%, 63.5%, 64.0%, 64.5%, 65.0%, 65.5%, 66.0%, 66.5%, 67.0%, 67.5%, 68.0%, 68.5%, 69.0%, 69.5%, 70.0%, 70.5%, 71.0%, 71.5%, 72.0%, 72.5%, 73.0%, 73.5%, 74.0%, 74.5%, 75.0%, 75.5%, 76.0%, 76.5%, 77.0%, 77.5%, 78.0%, 78.5%, 79.0%, 79.5%, 80.0%, 80.5%, 81%, 81.5%, 82%, 82.5%, 83%, 83.5%, 84%, 84.5%, and 85% *Aloe Vera*.

The amount of water in the delivery system generally depends on the amount of other reagents (e.g., delivered agent, penetration enhancer, and other aqueous adjuvants or fillers). Although water is used as the sole aqueous adjuvant in some embodiments, preferred embodiments use enough water to make the total volume of a particular preparation of a delivery system such that the desired concentrations of reagents in the penetration enhancer, aqueous adjuvant, and delivered agent are achieved. Suitable forms of water are deionized, distilled, filtered or otherwise purified. Clearly, however, any form of water can be used as an aqueous adjuvant.

Transdermal delivery systems having water can comprise between 0.1% to 85.0% by weight or volume water. That is, embodiments of the invention can comprise by weight or volume less than or equal to or greater than 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0% 8.25%, 8.5%, 8.75%, 9.0%, 9.25%, 9.5%, 9.75%, 10.0%, 10.25%, 10.5%, 10.75%, 11.0%, 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.25%, 40.5%, 40.75%, 41.0%, 41.25%, 41.5%, 41.75%, 42.0%, 42.25%, 42.5%, 42.75%, 43.0%, 43.25%, 43.5%, 43.75%, 44.0%, 44.25%, 44.5%, 44.75%, 45.0%, 45.25%, 45.5%, 45.75%, 46.0%, 46.25%, 46.5%, 46.75%, 47.0% 47.25%, 47.5%, 47.75%, 48.0%, 48.25%, 48.5%, 48.75%, 49.0%, 49.25%, 49.5%, 49.75%, 50.0%, 50.25%, 50.5%, 50.75%, 51.0%, 51.25%, 51.5%, 51.75%, 52.0%, 52.25%, 52.5%, 52.75%, 53.0%, 53.25%, 53.5%, 53.75%, 54.0%, 54.5%, 54.0%, 54.5%, 55.0%, 55.5%, 56.0%, 56.5%, 57.0%, 57.5%, 58.0%, 58.5%, 59.0%, 59.5%, 60.0%, 60.5%, 61.0%, 61.5%, 62.0%, 62.5%, 63.0%, 63.5%, 64.0%, 64.5%, 65.0%, 65.5%, 66.0%, 66.5%, 67.0%, 67.5%, 68.0%, 68.5%, 69.0%, 69.5%, 70.0%, 70.5%, 71.0%, 71.5%, 72.0%, 72.5%, 73.0%, 73.5%, 74.0%, 74.5%, 75.0%, 75.5%, 76.0%, 76.5%, 77.0%, 77.5%, 78.0%, 78.5%, 79.0%, 79.5%, 80.0%, 80.5%, 81%, 81.5%, 82%, 82.5%, 83%, 83.5%, 84%, 84.5%, and 85% water. In addition to the aforementioned compositions, methods of making and using the transdermal delivery systems are described in the following section.

Preparing Transdermal Delivery Systems

In general, transdermal delivery systems are prepared by combining a penetration enhancer with a delivered agent and, optionally, an aqueous adjuvant. Depending on the solubility of the delivered agent, the delivered agent can be solubilized in either the hydrophobic or hydrophilic components of the penetration enhancer. In some formulations, (e.g., formulations containing oil soluble delivered agents such as steroid hormones), the delivered agent readily dissolves in the ethoxylated oil without water, alcohol, or an aqueous adjuvant. In other formulations, the delivered agent (e.g., an NSAID or collagen or fragments thereof) readily dissolves in water, which is then mixed with the ethoxylated oil. Additionally, some delivered agents can be solubilized in the aqueous adjuvant prior to mixing with the penetration enhancer. Desirably, the pH of the mixture is maintained between 3 and 11 and preferably between 5 and 9. That is, during preparation and after preparation the pH of the solution is desirably maintained at less than or equal to 3.0, 3.25, 3.5, 3.75, 4.0, 4.25, 4.5, 4.75, 5.0, 5.25, 5.5, 5.75, 6, 6.25, 6.5, 6.75, 7.0, 7.25, 7.5, 7.75, 8.0, 8.25, 8.5, 8.75, 9.0, 9.25, 9.5, 9.75, 10.0, 10.25, 10.5, 10.75, or 11.0.

Several physical mixing techniques can be employed to help the delivery system coalesce. For example, a magnetic stir plate and bar can be used, however, the speed of stirring is preferably minimized so as not to drive air into the mixture and/or destroy the delivered agent (e.g., when the delivered agent is a peptide or a protein). Additionally, a rocker can be used to bring components of the delivery system together. Heat can also be applied to help coalesce the mixture but desirably, the temperature is not raised above 40° C. so that labile aqueous adjuvants or labile delivered agents are not degraded. Preferably, once the delivery system has coalesced, other components such as fragrances and colors are added or the delivery system is incorporated into a cream or ointment or a device for applying the delivery system.

Several formulations of delivery system are within the scope of aspects of the invention. Desirably, the ratio of hydrophilic component:hydrophobic component:aqueous adjuvant is 3:4:3, but preferred formulations comprise 1:1:4, 1:1:14, and 1:10:25. As described above, a sufficient amount of delivered agent to suit the intended purpose is incorporated into the delivery system. The amount of delivered agent that is incorporated into the penetration enhancer depends on the compound, desired dosage, and application.

In some embodiments, the transdermal delivery system is provided in a single dose application containing a pre-measured amount of the delivered agent. For example, septum sealed vials with or without an applicator (e.g., a swab) containing a pre-measured amount of transdermal delivery system (e.g., 0.5 ml) containing a pre-measured amount of a delivered agent (e.g., 400 mg of ibuprofen, 0.6 mg marine collagen, or 1 g of aspirin) are embodiments of the invention. These embodiments have significant utility because pre-determined doses of certain delivered agents facilitate appropriate treatment regimens and the individually sealed doses of the transdermal delivery system with delivered agent maintain sterility of the composition between applications.

In some embodiments, the transdermal delivery system is made by providing an ethoxylated oil, mixing the ethoxylated oil with an alcohol, non-ionic solubilizer, or emulsifier so as to form a penetration enhancer, mixing the penetration enhancer with an aqueous adjuvant (e.g., an extract from a plant of the Liliaeacae family), and mixing the penetration enhancer and aqueous adjuvant with a delivered agent and thereby making the transdermal delivery system. For example, an embodiment of a transdermal delivery system comprising a pain relief solution is manufactured as follows. A solution of 2.0% to 7.0% oleoresin capsicum, 2.5 grams of Boswellin is mixed with 400 ml of absolute carpilic alcohol or isopropyl alcohol, 300 ml of ethoxylated castor oil, and 300 ml of a 100% solution of *Aloe Vera*. This transdermal delivery system has been observed to alleviate pain when rubbed on a targeted area.

The transdermal delivery systems having a form of Hepsyl as a delivered agent desirably are comprised by weight or volume of between 0.005% to 12.0% Hepsyl, depending on the type of Hepsyl, its solubility, and the intended application. For example, embodiments having Hepsyl CA 1501C. Hepsyl CGA 1501K., and Hepsyl RA 150K can be comprised by weight or volume of 0.01-2 grams of Hepsyl delivered agent, 0-50 mL of hydrophobic penetration enhancers (e.g., ethoxylated castor oil, jojoba oil, etc.), 0-50 mL of hydrophilic penetration enhancers, nonionic solubilizers, or emulsifiers (e.g., isopropyl. alcohol, DMSO, etc.), and 0-50 mL of aqueous adjuvant (e.g., water, *Aloe Vera* extract, etc.). A particularly desirable embodiment of the invention is comprised of 0.1-0.5 gram of Hepsyl, 5-10 mL of ethoxylated castor oil, 5-10 mL of isopropyl alcohol, and 5-10 mL of *Aloe Vera* extract. By using these formulations, other delivered agents can be incorporated into a transdermal delivery system. Formulations of transdermal delivery systems having collagens are described in the examples. The following section describes several therapeutic, prophylactic and cosmetic applications.

Therapeutic, Prophylactic, and Cosmetic Applications

Many embodiments are suitable for treatment of subjects either as a preventive measure (e.g., to avoid pain or skin disorders) or as a therapeutic to treat subjects already afflicted with skin disorders or who are suffering pain. In general, most drugs, chemicals, and cosmetic agents that can be incorporated into a pharmaceutical or cosmetic can be formulated into a transdermal delivery system of the invention. Because the various formulations of transdermal delivery system described herein have a considerable range in hydrophobic and hydrophilic character, most drugs, chemicals, and cosmetic preparations can be incorporated therein. That is, by adjusting the amount of ethoxylation, alcohol, and water in a particular formulation most pharmaceutical and cosmetic agents are solubilized in a transdermal delivery system with little effort. Furthermore, because the transdermal delivery systems described herein can deliver a wide range of materials of both high and low molecular weight to skin cells, the utility of the transdermal delivery systems described herein is incredibly broad. The aspects of the invention that follow are for exemplary purposes only, and one of skill in the art can readily appreciate the wide spread applicability of a transdermal delivery system described herein and the incorporation of other delivered agents into a formulation of transdermal delivery system is straight forward.

In one embodiment, for example, a method of treatment or prevention of inflammation, pain, or human diseases, such as cancer, arthritis, and Alzheimer's disease, comprises using a transdermal delivery system described herein that has been formulated with an NSAID. Because delivered agents such as NSAIDs, capsaicin, and Boswellin interfere and/or inhibit cyclooxygenase enzymes (COX-1 and COX-2), they provide a therapeutically beneficial treatment for cancer and Alzheimer's disease when administered by a transdermal delivery system described herein. (See U.S. Pat. No. 5,840,746 to Ducharme et al., and U.S. Pat. No. 5,861, 268 to Tang et al.).

By one approach, a transdermal delivery system comprising a delivered agent that is effective at reducing pain or inflammation (e.g., NSAIDS, capsaicin, Boswellin, or any combination thereof) is administered to a subject in need and the reduction in pain or inflammation is monitored. An additional approach involves identifying a subject in need of a COX enzyme inhibitor (e.g., a subject suffering from cancer or Alzheimer's disease) and administering a transdermal delivery system comprising a delivered agent that inhibits a COX enzyme (e.g., NSAIDS, capsaicin, Boswellin, or any combination thereof). Although many individuals can be at risk for contracting cancer or Alzheimer's disease, those with a family history or a genetic marker associated with these maladies are preferably identified. Several diagnostic approaches to identify persons at risk of developing these diseases have been reported. (See e.g., U.S. Pat. Nos., 5,891,857; 5,744,368; 5,891,651; 5,837, 853; and 5,571,671). The transdermal delivery system is preferably applied to the skin at a region of inflammation or an area associated with pain or the particular condition and treatment is continued for a sufficient time to reduce inflammation, pain, or inhibit the progress of the disease. Typically, pain and inflammation will be reduced in 5-20 minutes after application. Cancer and Alzheimer's disease can be inhibited or prevented with prolonged use.

In another method, an approach to reduce wrinkles and increase skin tightness and flexibility (collectively referred to as "restoring skin tone") is provided. Accordingly, a transdermal delivery system comprising a form of collagen or fragment thereof as a delivered agent is provided and contacted with the skin of a subject in need of treatment. By one approach, a subject in need of skin tone restoration is identified, a transdermal delivery system comprising collagen or a fragment thereof is administered to the subject, and the restoration of the skin tone is monitored. Identification of a person in need of skin restoration can be based solely on visible inspection and the desire to have tight, smooth, and flexible skin. Treatment with the delivery system is continued until a desired skin tone is achieved. Typically a change in skin tone will be visibly apparent in 15 days but prolonged use may be required to retain skin tightness and flexibility. The form of collagen in the delivered agent can be from various sources and can have many different molecular weights, as detailed above. Preferably, high molecular weight natural collagens are used, however, recombinant collagens, modified collagens, protease resistant collagens, and fragments thereof may be used with some of the transdermal delivery systems described herein.

The transdermal delivery systems described herein can be processed in accordance with conventional pharmacological and cosmetological methods to produce medicinal agents and cosmetics for administration to patients, e.g., mammals including humans. The transdermal delivery systems described herein can be incorporated into a pharmaceutical or cosmetic product with or without modification. The compositions of the invention can be employed in admixture with conventional excipients, e.g., pharmaceutically acceptable organic or inorganic carrier substances suitable for topical application that do not deleteriously react with the molecules that assemble the delivery system. The preparations can be sterilized and if desired mixed with auxiliary agents, e.g., lubricants, preservatives, stabilizers, coloring, aromatic substances and the like that do not deleteriously react with the active compounds. They can also be combined where desired with other active agents.

The effective dose and method of administration of a carrier system formulation can vary based on the individual patient and the stage of the disease, as well as other factors known to those of skill in the art. Although several doses of delivered agents have been indicated above, the therapeutic efficacy and toxicity of such compounds in a delivery system of the invention can be determined by standard pharmaceutical or cosmetological procedures with experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical and cosmetological compositions that exhibit large therapeutic indices are preferred. The data obtained from animal studies is used in formulating a range of dosages for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease state, age, weight and gender of the patient; diet, time and frequency of administration, drug combination(s), reaction sensitivities, and tolerance/response to therapy. Short acting compositions are administered daily whereas long acting pharmaceutical compositions are administered every 2, 3 to 4 days, every week, or once every two weeks. Depending on half-life and clearance rate of the particular formulation, the pharmaceutical compositions of the invention are administered once, twice, three, four, five, six, seven, eight, nine, ten or more times per day.

Routes of administration of the delivery systems of the invention are primarily topical, although it is desired to administer some embodiments to cells that reside in deep skin layers. Topical administration is accomplished via a topically applied cream, gel, rinse, etc. containing a delivery system of the invention. Compositions of delivery system-containing compounds suitable for topical application include, but are not limited to, physiologically acceptable ointments, creams, rinses, and gels.

In some embodiments, the mixture of penetration enhancer, aqueous adjuvant, and delivered agent is incorporated into a device that facilitates application. These apparatus generally have a vessel joined to an applicator, wherein a transdermal delivery system of the invention is incorporated in the vessel. Some devices, for example, facilitate delivery by encouraging vaporization of the mixture. These apparatus have a transdermal delivery system of the invention incorporated in a vessel that is joined to an applicator such as a sprayer (e.g., a pump-driven sprayer). These embodiments can also comprise a propellant for driving the incorporated transdermal delivery system out of the vessel. Other apparatus can be designed to allow for a more focused application. A device that facilitates a focused application of a transdermal delivery system of the invention can have a roll-on or swab-like applicator joined to the vessel that houses the transdermal delivery system. Several devices that facilitate the administration of a delivery system of the invention have a wide range of cosmetic or therapeutic applications. The example below describes a clinical study that was performed to evaluate the efficacy of a transdermal delivery system that comprised capsaicin.

EXAMPLE 1

In this example, evidence is provided that a transdermal delivery system of the invention can administer a therapeutically effective amount of a low molecular weight delivered agent (e.g., 0.225% oleoresin capsicum). A clinical study was performed to evaluate the effectiveness of a transdermal delivery system of the invention comprising 0.225% capsaicin ("EPRS") as compared to a commercially available cream comprising Boswellin, 10% methyl salicylate, and 0.25% capsaicin. (Nature's Herbs). The two pain relief preparations were tested on six subjects who suffer from degenerative arthritis, debilitating back pain, and/or bursitis. For the first five days of the study, the subjects applied the commercially available cream three times a day. On day six, application of the commercially available cream was stopped and subjects applied the EPRS transdermal delivery system. The EPRS pain relief solution was also applied for five days, three times a day. Daily analysis of the efficacy of the particular pain relief formulations was taken by the subjects and observations such as the time of administration, odor, and therapeutic benefit were recorded after each administration.

The five day use of the commercially available cream was found to provide only minimal therapeutic benefit. The cream was reported to irritate the skin, have a noxious smell, and provide little decrease in pain or increase in flexibility or range of motion. In contrast, the five day use of EPRS was reported to provide significant pain relief, relative to the relief obtained from the oral consumption of NSAIDs. Further, EPRS was reported to increase flexibility and range of motion within five to twenty minutes after application. Additionally, EPRS did not present a significant odor nor did it cause skin irritation. The results of this study demonstrate that a delivery system comprising a low molecular weight compound, capsaicin, can effectively administer the delivered agent to cells of the body where it provides therapeutic benefit. The next example describes a clinical study that was performed to evaluate the efficacy of several different formulations of transdermal delivery system that comprised low and high molecular weight collagens.

EXAMPLE 2

In this example, evidence is provided that a transdermal delivery system of the invention can administer a therapeutically effective amount of a low and high molecular weight delivered agent (e.g., a low and high molecular weight collagens). A clinical study was performed to evaluate the effectiveness of several transdermal delivery systems comprising various penetration enhancers, aqueous adjuvants, and collagen delivered agents. The various transdermal delivery systems that were evaluated are provided in TABLE 18. Of the formulations that were originally screened, three were extensively evaluated by ten subjects (three men and seven women) in a single blind study. The formulations analyzed in the single blind study are indicated in TABLE 18 by a dagger. That is, the three different formulations ("P1", "P2", and "F4") were evaluated.

The P1 formulation comprised approximately 0.73% to 1.46% Solu-Coll, a soluble collagen having a molecular weight of 300,000 daltons. The P2 formulation comprised approximately 1.43% to 2.86% Plantsol, a plant collagen obtained from yeast having a molecular weight of 500,000 daltons. The F4 formulation comprised approximately 11.0% of HydroColl EN-55, a hydrolyzed collagen having a molecular weight of 2,000 daltons. The evaluation of the P1, P2, and F4 formulations was as follows. Left, right, and center mug-shot photographs were taken with a Pentax camera having a zoom 60× lens and Kodak-Gold 100 film before beginning the study. Shortly after, each subject was given a bottle having a formulation of transdermal delivery system and was instructed to apply the solution to the right side of the face and neck, leaving the left side untreated, twice daily for 15 days. The F4 formulation was tested first and the application was carried out after showering or washing and before application of any other product to the treated area of the face. After the 15 day period, three mug-shot photographs were again taken, the subjects recorded their observations on the effectiveness of the formulation in a questionnaire, and a 7 day period without application of a collagen product provided. The questionnaire requested the subject to assign a score (e.g., a numerical value that represents effectiveness) on characteristics of the transdermal delivery system formulation. Characteristics that were evaluated included tackiness, odor, marketability, and overall effectiveness of the formulation, as well as, whether the formulation tightened the skin, decreased lines, conditioned or softened the skin, and had any negative side-effects. The scale for the scoring was 1-10, with 1 being the worst rating and 10 being the best rating.

Following the test of F4, the evaluation detailed above was conducted on the P1 formulation. Again, photographs were taken before and after the second 15 day protocol, a questionnaire evaluating the efficacy of the particular formulation was completed, and a 7 day period without application of a collagen product was provided. Further, after the test of P1, the same evaluation was conducted on the P2 formulation, photographs were taken before and after the trial, and a questionnaire evaluating the efficacy of the particular formulation was completed.

The data from the three evaluation questionnaires were pooled, analyzed using a "t-table" and standard deviation calculations were made. See TABLE 19. An overall rating for each particular formulation was assigned. A perfect score by this system was a 7.875 overall rating. P1 was found to have a 4.25 overall rating (approximately 54% effective), P2 was found to have a 4.625 overall rating (approximately 59% effective), and F4 was found to have a 5.625 overall rating (approximately 71% effective).

The before and after treatment photographs also revealed that the three tested transdermal delivery systems provided therapeutic benefit. A decrease in wrinkles was observed and an increase in skin tightness and firmness can be seen. That is, P1, P2, and F4 all provided therapeutic and/or cosmetic benefit in that they restored skin tone in the subjects tested. The results presented above also demonstrate that transdermal delivery systems of the invention can be used to administer high molecular weight delivered agents.

TABLE 18

| ECO | Aloe | IPA | Plantsol | EN-55 | Solu-coll | DMPX | YYO | Score | ID |
|---|---|---|---|---|---|---|---|---|---|
| 29.7%* | 50.0%* | 5.0%* | 0* | 8.3%* | 0* | 0* | 0* | 2 | F-1 |
| 10.4% | 79.0% | 5.3% | 0 | 8.7% | 0 | 0 | 0 | 3 | F-2 |
| 5.2% | 63.0% | 5.3% | 0 | 17.4% | 0 | 0 | 0 | 3 | F-3 |
| 5.0% | 70.0% | 5.0% | 0 | 11.0% | 0 | 0 | 0 | 3+ | F-4 † |
| 4.5% | 18.2% | 4.6% | 0 | 0 | 0.7% to 1.5% | 0 | 0 | 3+ | P-1 † |
| 8.3% | 8.3% | 8.3% | 0.7% to 1.4% | 4.6% | 0.3% to 0.7% | 0 | 0 | 2 | Y-500 |
| 0.7% | 22.2% | 11.1% | 1.3% to 2.7% | 0 | 0 | 0 | 0 | 3+ | P-501 |
| 0.4% | 35.7% | 3.6% | 1.1% to 2.1% | 0 | 0 | 0 | 0 | 2 | P-502 |
| 0.9% | 8.7% | 0 | 0 | 0 | 2.3% to 4.6% | 0 | 0 | 1 | SC-1 |
| 1.8% | 18.5% | 0 | 0 | 44.8% | 0 | 0 | 0 | 3+ | SC-2 |
| 1.8% | 17.9% | 7.1% | 0 | 43.2% | 0 | 0 | 0 | 3 | SC-3 |
| 0.9% | 9.4% | 4.7% | 0 | 34.3% | 0.3% to 0.6% | 0 | 0 | 1 | PSCEN |
| 1.8% | 31.3% | 6.3% | 0.3% to 2.5% | 0 | 0 | 0 | 0 | 3+ | P-1A |
| 0.8% | 19.2% | 3.8% | 1.5% to 3.1% | 0 | 0 | 7.7% | 0.3% | 5 | P-1C |
| 0.7% | 17.9% | 7.1% | 1.4% to 2.9% | 0 | 0 | 1.1% | 0.3% | 5 | P-2 † |

TABLE 18-continued

| ECO | Aloe | IPA | Plantsol | EN-55 | Solu-coll | DMPX | YYO | Score | ID |
|---|---|---|---|---|---|---|---|---|---|
| 0.7% | 22.2% | 11.1% | 1.3% to 2.7% | 0 | 0 | 0 | 0 | 3+ | P-501 |

Abbreviations:
ECO—ethoxylated castor oil (BASF)
Aloe—Aloe Vera (Aloe Labs; (800)-258-5380)
IPA—Absolute isopropyl alcohol (Orange County Chemical, Santa Ana, California)
Plantsol—Yeast extract collagen (Brooks Industries Inc., Code No. 06485)
EN-55—hydrolyzed bovine collagen (Brooks Industries Inc., Code No. 01000)
SoluColl—soluble collagen (Brooks Industries Inc., Code No. 01029)
DMPX—dimethyl polysiloxane (5 centistokes) (Sigma)
YYO—Y-ling-Y-lang oil (Young Living Essential Oils, Lehl, Utah)
ID—Identification number
*The percentages reflect volume to volume.
† Sample used in the 45 day clinical trial.

TABLE 19

Collagen T-Table

| Formulations | P1 | P2 | F4 | standard deviation |
|---|---|---|---|---|
| Tackiness | 5 | 3 | 10 | 2.94 |
| Skin tightness | 7 | 5 | 8 | 1.25 |
| Odor | 2 | 8 | 8 | 2.83 |
| Decrease lines | 2 | 2 | 1 | 0.47 |
| Soften skin | 8 | 7 | 4 | 1.7 |
| Total skin restoration | 5 | 5 | 6 | 0.47 |
| Market Buying Power | 5 | 7 | 8 | 1.25 |
| Side effects | 0 | 0 | 0 | 0 |
| Total Score (Average) | 4.25 | 4.63 | 5.63 | 1.36 |

Several in vitro techniques are now widely used to assess the percutaneous absorption of delivered agents. (See e.g., Bronaugh and Collier in *In vitro Percutaneous absorption studies: Principle, Fundamentals, and Applications*, eds. Bronaugh and Maibach, Boca Raton, Fla., CRC Press, pp 237-241 (1991) and Nelson et al., *J. Invest. Dermatol.* 874-879 (1991), herein incorporated by reference in its entirety). Absorption rates, and skin metabolism can be studied in viable skin without the interference from systemic metabolic processes. The next example describes several approaches that can be used to evaluate the ability of a particular formulation of transdermal delivery system to deliver a particular delivered agent.

EXAMPLE 3

Skin barrier function can be analyzed by examining the diffusion of fluorescent and colored proteins and dextrans of various molecular weights ("markers") across the skin of nude mice or swine. Swine skin is preferred for many studies because it is inexpensive, can be maintained at −20° C., and responds similarly to human skin. Prior to use, frozen swine skin is thawed, hair is removed, and subcutaneous adipose tissue is dissected away. Preferably, a thickness of skin that resembles the thickness of human skin is obtained so as to prepare a membrane that accurately reflects the thickness of the barrier layer. A dermatome can be pushed across the surface of the skin so as to remove any residual dermis and prepare a skin preparation that accurately reflects human skin. Elevation of temperature can also be used to loosen the bond between the dermis and the epidermis of hairless skin. Accordingly, the excised skin is placed on a hot plate or in heated water for 2 minutes at a temperature of approximately 50° C.-60° C. and the dermis is removed by blunt dissection. Chemical approaches (e.g., 2M salt solutions) have also been used to separate the dermis from the epidermis of young rodents.

Many different buffers or receptor fluids can be used to study the transdermal delivery of delivered agents across excised skin prepared as described above. Preferably, the buffer is isotonic, for example a normal saline solution or an isotonic buffered solution. More physiological buffers, which contain reagents that can be metabolized by the skin, can also be used. (See e.g., Collier et al., *Toxicol. Appl. Pharmacol.* 99:522-533 (1989)).

Several different markers with molecular weight from 1,000 daltons to 2,000,000 daltons are commercially available and can be used to analyze the transdermal delivery systems of the invention. For example, different colored protein markers having a wide range of molecular weights (6,500 to 205,000 daltons) and FITC conjugated protein markers (e.g., FITC conjugated markers from 6,500 to 205,000 daltons) are available from Sigma (C3437, M0163, G7279, A2065, A2190, C1311, T9416, L8151, and A2315). Further, high molecular weight FITC conjugated dextrans (e.g., 250,000, 500,000, and 2,000,000 daltons) are obtainable from Sigma. (FD250S, FD500S, and FD2000S).

Accordingly, in one approach, swine skin preparations, obtained as described above, are treated with a delivery system lacking a delivered agent and control swine skin preparations are treated with water. Subsequently, the skin is contacted with a 1 mM solution of a marker with a known molecular weight suspended in Ringer's solution (pH 7.4) at 37° C. After one hour, the skin is frozen and sliced at a thickness of 5 μm. The sections are counter stained with 5 μg/ml propidium and, if the marker is FITC conjugated, the sections are analyzed by fluoresence microscopy. If the marker is a colored marker, diffusion of the marker can be determined by light microscope. The marker will be retained in the upper layers of the stratum corneum in the untreated mice but the delivery system treated mice will be found to have the dye distributed throughout the stratum corneum and any dermal layer that remains.

Additionally, modifications of the experiments described above can be performed by using a delivery system comprising various molecular weight markers. Accordingly, skin preparations are treated with the delivery system comprising one or more markers and control skin preparations are treated with water. After one hour, the skin is frozen and sliced at a thickness of 5 μm. The sections can be counter stained with 5 μg/ml propidium iodide and can be analyzed by fluoresence microscopy (e.g., when a fluorescent marker is used) or alternatively, the sections are analyzed under a light microscope. The various markers will be retained in the upper layers of the stratum corneum in the untreated mice but the delivery system treated mice will be found to have the marker distributed throughout the stratum corneum and any dermal layer that remains.

In another method, the transdermal water loss (TEWL) of penetration enhancer-treated skin preparations can be compared to that of untreated skin preparations. Accordingly, skin preparations are obtained, as described above, and are treated with a delivery system of the invention lacking a delivered agent (e.g., a penetration enhancer). Control skin preparations are untreated. To assess TEWL, an evaporimeter is used to analyze the skin preparation. The Courage and Khazaka Tewameter TM210, an open chamber system with two humidity and temperature sensors, can be used to measure the water evaporation gradient at the surface of the skin. The parameters for calibrating the instrument and use of the instrument is described in Barel and Clarys *Skin Pharmacol.* 8: 186-195 (1995) and the manufacturer's instructions. In the controls, TEWL will be low. In contrast, TEWL in penetration enhancer-treated skin preparations will be significantly greater.

Further, skin barrier function can be analyzed by examining the percutaneous absorption of labeled markers (e.g., radiolabeled, fluorescently labeled, or colored) across skin preparations in a diffusion chamber. Delivery systems of the invention having various molecular weight markers, for example, the proteins and dextrans described above, are administered to swine skin preparations. Swine skin preparations are mounted in side-by-side diffusion chambers and are allowed to stabilize at 37° C. with various formulations of penetration enhancer. Donor and receiver fluid volumes are 1.5 ml. After 1 hour of incubation, a labeled marker is added to the epidermal donor fluid to yield a final concentration that reflects an amount that would be applied to the skin in an embodiment of the invention. Five hundred microliters of receiver fluid is removed at various time points, an equal volume of penetration enhancer is added to the system. The aliquot of receiver fluid removed is then analyzed for the presence of the labeled marker (e.g., fluorescent detection, spectroscopy, or scintillation counting). Control swine skin preparations are equilibrated in Ringer's solution (pH 7.4) at 37° C.; the same concentration of labeled marker as used in the experimental group is applied to the donor fluid after one hour of equilibration; and 500 μl of receiver fluid is analyzed for the presence of the marker. In the experimental group, the steady-state flux of labeled marker in the skin will be significantly greater than that of the control group. By using these approaches, several transdermal delivery systems can be evaluated for their ability to transport low and high molecular weight delivered agents across the skin. The next example describes several different formulations of transdermal delivery system that were made to comprise various delivered agents, demonstrating the wide-range of utility of aspects of the invention.

EXAMPLE 4

In this example, several different formulations of transdermal delivery system containing various delivered agents are provided. The formulations described include: compositions for removing age spots and restoring skin brightness, compositions for advanced pain relief, muscle relaxers, hormone replacement products, wound healing formulations, products for reducing fine lines and wrinkles, stretch mark reducing products, growth factor products, and anti-psoriasis products.

| Skin brightening or age spot reducing product: | |
|---|---|
| Melaslow (10%) | 30 ml |
| Ethoxylated Macadamia nut oil (16 ethoxylations/molecule) | 160 ml |
| Ethanol | 80 ml |
| Water | 40 ml |
| Marine collagen (1%) | 40 ml |
| Etioline (5%) | 30 ml |

This formulation was found to rapidly reduce the appearance of age spots in a subject that applied daily amounts of the product for thirty days.

| Stretch Mark Reducing products: | |
|---|---|
| Formulation #1 | |
| *Eucalyptus* oil | 400 ml |
| Ethanol | 180 ml |
| Ethoxylated *macadamia* nut oil (16 ethoxylations/molecule) | 180 ml |
| Distilled water | 40 ml |
| various perfumes were added including | |
| lemon oil or | 30 drops |
| lavender or | 30 drops |
| sweet orange or | 1 ml |
| tangerine | 30 drops |
| Formulation #2 | |
| *Eucalyptus* oil | 500 ml |
| Ethanol | 225 ml |
| Ethoxylated *macadamia* nut oil (16 ethoxylations/molecule) | 225 ml |
| Distilled water | 50 ml |
| Formulation #3 | |
| *Eucalyptus* oil (Kayuuputih oil) | 400 ml |
| Ethanol | 220 ml |
| Ethoxylated *macadamia* nut oil (16 ethoxylations/molecule) | 180 ml |
| Distilled water | 40 ml |
| Y-Ling-Y-Lang | 22 drops |
| Coconut oil | 3 ml |

These formulations were found to rapidly reduce the appearance of stretch marks in a subject that applied daily amounts of the products for thirty days.

| Testosterone Supplementation Products: | |
|---|---|
| Formulation #1 | |
| Ethanol | 30 ml |
| Ethoxylated *macadamia* nut oil (16 ethoxylations/molecule) | 30 ml |
| Water | 20 ml |
| Testosterone | 10 ml (200 mg/ml) |
| Coconut oil | 10 drops |
| Formulation #2 | |
| Ethanol | 40 ml |
| Ethoxylated *macadamia* nut oil (16 ethoxylations/molecule) | 40 ml |
| Water | 5 ml |

Testosterone Supplementation Products:

| | |
|---|---|
| Testosterone | 5 ml (200 mg/ml) |
| Coconut oil | 10 drops |
| Y-Ling-Y-Lang oil | 10 drops |

Formulation #3

| | |
|---|---|
| Testosterone | 10 ml (200 mg/ml) |
| Ethanol | 40 ml |
| Ethoxylated *macadamia* nut oil (16 ethoxylations/molecule) | 40 ml |
| Coconut oil | 10 drops |
| Y-Ling-Y-Lang oil | 10 drops |
| Water | 3 ml |

Formulation #4

| | |
|---|---|
| Testosterone | 1,000 mg in 5 ml |
| Ethanol | 50 ml |
| Ethoxylated *macadamia* nut oil (16 ethoxylations/molecule) | 40 ml |
| Water | 5 ml |
| Y-Ling-Y-Lang oil | 15 drops |
| Rain water | 15 drops |

These formulations were found to rapidly increase the amount of testosterone in the blood of a subject that applied approximately 0.5 ml of the product daily.

Pain Relief Products:

Formulation #1

| | |
|---|---|
| Ethyl alcohol | 10.4 g |
| White willow bark extract | 10.4 g |
| Glucosamine HCL | 10 g |
| MSM | 10 g |
| Chrondroitan sulfate sodium | 10 g |
| Marine collagen (1%) | 100 ml |
| *Aloe Vera* (whole leaf) concentrate | 100 ml |
| Ethoxylated *macadamia* nut oil (16 ethoxylations/molecule) | 300 ml |
| Y-Ling-Y-Lang oil | 28 drops |
| Coconut oil | 3 ml |
| Ibuprofen | 16 g |

Formulation #2

| | |
|---|---|
| Ibuprofen | 3 g |
| Methocarbanol | 3 g |
| Chlorzoxazone | 5 g |
| Ethanol | 75 ml |
| *Macadamia* nut oil (16 ethoxylations/molecule) | 75 ml |
| *Aloe Vera* (whole leaf) concentrate | 5 ml |
| Y-Ling-Y-Lang oil | 10 drops |

Compounds brought into solution with slight heat.

Formulation #3

| | |
|---|---|
| Acetyl salicylic acid | 22 g |
| Ibuprofen | 8.5 g |
| Ethanol (undenatured) | 500 ml |
| Ethoxylated *macadamia* nut oil (16 ethoxylations/molecule) | 400 ml |
| Distilled water | 100 ml |
| Peppermint oil | 20 drops |

Formulation #4

| | |
|---|---|
| Acetyl salicylic acid | 44 g |
| Undenatured ethanol | 800 ml |
| Ethoxylated *macadamia* nut oil (16 ethoxylations/molecule) | 200 ml |
| Distilled water | 40 drops |
| Y-ling Y-lang oil | 40 drops |
| Peppermint oil | 40 drops |

Formulation #5

| | |
|---|---|
| Acetyl salicylic acid | 44 g |
| Undenatured ethanol | 900 ml |
| Ethoxylated *macadamia* nut oil (16 ethoxylations/molecule) | 1000 ml |
| Distilled water | 100 ml |
| Y-ling y-lang oil | 40 drops |
| Peppermint oil | 40 drops |

Formulation #6

| | |
|---|---|
| Liquid aspirin | 44 g |
| Undenatured ethanol | 800 ml |
| Ethoxylated *macadamia* nut oil (16 ethoxylations/molecule) | 200 ml |
| Distilled water | 40 drops |
| Y-ling y-lang oil | 20 drops |
| Peppermint oil | 40 drops |

These formulations were found to reduce pain in several subjects within 5-20 minutes after application. Depending on the formulation, the period of pain reduction lasted from 45 minutes (e.g., acetyl salicylic acid preparations) to several hours (e.g., ibuprofen containing preparations).

Skin care/anti-psoriasis/anti-eczema/wound healing Products:
Formulation #1

| | |
|---|---|
| Dmae bitartrate | 22.5 g |
| Alpha lipoic acid | 5 g |
| Ethyl alcohol | 25 ml |
| Marine collagen (1%) | 25 ml |
| *Aloe Vera* | 25 ml |
| *Macadamia* nut oil (16 ethoxylations/molecule) | |

The Dmae bitartrate and alpha lipoic acid was brought into solution and filtered prior to mixture with the ethoxylated macadamia nut oil.

Formulation #2

| | |
|---|---|
| Ichtyocollagene (1%) | 500 ml |
| Distilled water | 248 ml |
| LKEKK (SEQ. ID. No. 1) | 1 vial (about 1 ml~10 μg) |
| Ethoxylated *macadamia* nut oil (16 ethoxylations/molecule) | 150 ml |
| Ethanol | 25 ml |
| Phenochem (i.e., a mixture of Methyl Paraben, Ethyl Paraben, Propyl Paraben, Butyl Paraben, and Isobutyl Paraben) | 39 ml |

Formulation #3

| | |
|---|---|
| Distilled water | 100 ml |
| LKEKK (SEQ. ID. No. 1) | bottles (~50 μg) |
| Ethoxylated *macadamia* nut oil (16 ethoxylations/molecule) | 40 ml |
| Ethanol | 5 ml |

These formulations were found to improve the healing of a wound (a laceration) and were found to reduce psoriasis and eczema in an afflicted subject.

| Products that Reduce the Appearance of Fine Lines and Wrinkles | |
|---|---|
| Formulation #1 | |
| Ichtyocollagene (1%) | 2,990 ml |
| Distilled water | 1,483 ml |
| Ethoxylated Macadamia nut oil (16 ethoxylations/molecule) | 922 ml |
| Ethanol | 150 ml |
| Matrixyl (8%) | 236 ml |
| Phenochem | 236 ml |
| Ethoxydiglycol | 33 ml |
| Formulation #2 | |
| Ichtyocollagene (6%) | 250 ml |
| Distilled water | 124 ml |
| Ethoxylated macadamia nut oil (16 ethoxylations/molecule) | 78 ml |
| Phenochem | 20 ml |
| Bio-ten (Atrium Biotechnologies, Inc., Quebec, Canada) | 1 ml |
| Ethanol | 10 ml |
| Formulation #3 | |
| Ichtyocollagene (1%) | 500 ml |
| Distilled water | 250 ml |
| Ethoxylated macadamia nut oil (16 ethoxylations/molecule) | 125 ml |
| Ethanol | 2 ml |
| Bio-ten | 3 ml |
| Phenochem | 40 ml |
| Formulation #4 | |
| Ichtyocollagene (1%) | 2,990 ml |
| Distilled water | 1,483 ml |
| Ethoxylated macadamia nut oil (16 ethoxylations/molecule) | 922 ml |
| Ethyl alcohol | 150 ml |
| Matrixyl | 236 ml |
| Phenochem | 236 ml |
| Formulation #5 | |
| Ichtyocollagene (1%) | 1,994 ml |
| Distilled water | 999 ml |
| Ethoxylated macadamia nut oil (16 ethoxylations/molecule) | 675 ml |
| Ethanol | 100 ml |
| Bioserum (Atrium Biotechnologies, Inc., Quebec, Canada) | 24 ml |
| Phenochem | 157 ml |
| Formulation #6 | |
| Ichtyocollagene (1%) | 500 ml |
| Distilled water | 250 ml |
| Ethoxylated macadamia nut oil (16 ethoxylations/molecule) | 168.75 ml |
| Ethanol | 25 ml |
| Bioserum | 10 ml |
| Phenochem | 43.75 ml |
| Formulation #7 | |
| Ichtyocollagene (1%) | 1,000 ml |
| Ethoxylated macadamia nut oil (16 ethoxylations/molecule) | 338 ml |
| Distilled water | 500 ml |
| Ethanol | 50 ml |
| Matrixyl | 76 ml |
| Phenochem | 76 ml |
| Formulation #8 | |
| Ichtyocollagene (1%) | 22.55 ml |
| Distilled Water | 11.7 ml |
| Ethoxylated macadamia nut oil (16 ethoxylations/molecule) | 7 ml |
| Phenochem | 0.5 ml |
| Ethanol | 1.5 ml |
| Bio Serum | 1 ml |
| TOTAL | 44.25 ml |
| Formulation #9 | |
| Ichtyocollagene (1%) | 15.03 ml |
| Distilled Water | 7.8 ml |
| Ethoxylated macadamia nut oil (16 ethoxylations/molecule) | 4.67 ml |
| Phenochem | 0.333 ml |
| Ethanol | 1 ml |
| Bio Serum | 0.67 ml |
| TOTAL | 29.5 ml |

These formulations were found to reduce the appearance of fine lines and wrinkles in subjects that applied the formulations daily for thirty days. It should be noted that Bioserum, which is obtainable from Atrium Biosciences, Ontario Canada, may contain one or more of the following: placental protein, amniotic fluid, calf skin extract, and serum protein. Also, phenochem may contain one or more of the following: Methyl Paraben, Ethyl Paraben, Propyl Paraben, Butyl Paraben, and Isobutyl Paraben, and sodium methylparaban imidizolidinyl urea. Additional components that may be included in some formulations of products that reduce the appearance of fine lines and wrinkles include: igepal cephene distilled, synasol, ethoxylated glycerides, trisodium EDTA, potassium sorbate, citric acid, ascorbic acid, and distilled water. For example, one formulation contains: Collagen (Marine), Distilled Water, Igepal Cephene Distilled, Methyl Paraben, Ethyl Paraben, Propyl Paraben, Butyl Paraben, Isobutyl Paraben, Synasol, Serum Protein, Purified Water, Amniotic Fluid. Placental Protein. Calfskin Extract, Hydrolyzed Collagen Sodium Methylparaben Imidazolidinyl Urea. Ethoxylated Glycerides, Trisodium EDTA, Potassium Sorbate, Citric Acid, and Ascorbic Acid. The following example describes experiments that employed two different skin cell model systems to evaluate the ability of a transdermal delivery system containing collagen to transport collagen to skin cells.

EXAMPLE 5

In this example, it is shown that a transdermal delivery system of the invention comprising marine type 1 collagen or native collagen efficiently transported the delivered agent to skin cells. Two different in vitro skin cell model systems were used, human cadaver skin and a cellulose acetate skin cell model system. Based on the physiology of the skin, three possible pathways exist for passive transport of molecules through the skin to the vascular network: (1) intercellular diffusion through the lipid lamellae; (2) transcellular diffusion through both the keratinocytes and lipid lamellae; and (3) diffusion through appendages (hair follicles and sweat ducts). The cellulose acetate skin model evaluates the ability of the delivered agent to transport using the first two pathways and the human cadaver skin evaluates the ability to use all three pathways.

In brief, the transdermal delivery system comprising collagen was applied to the cellulose acetate and the human cadaver skin in a diffusion chamber and the results were recorded after 10 minutes, 30 minutes and one hour. The diffused material was analyzed by a spectrophotometer (Hitachi U2000 multiscan spectrophotometer). A portion of the diffused material was also separated on a gel by electrophoresis and the collagen was stained using a collagen-specific dye. A portion of the diffused material was also immunoprecipitated using polyclonal antibodies specific for collagens types 1-7 and the immunoprecipitates were analyzed by immunodiffusion.

The table below provides the collagen concentration in the various samples of transdermal delivery systems tested. The protein concentration was determined using a micro-protein assay (Bio-Rad).

TABLE 20

| Sample number | Protein Concentrations | |
|---|---|---|
| | Native type 1 Collagen | Marine type 1 collagen |
| Sample 1 | 0.40 mg/ml | 1.14 mg/ml |
| Sample 2 | 0.44 mg/ml | 1.09 mg/ml |
| Sample 3 | 0.42 mg/ml | 1.14 mg/ml |
| Average | 0.42 | 1.12 |
| Standard error | 0.011 | 0.017 |
| Variance | 0.0004 | 0.0008 |
| Standard deviation | 0.02 | 0.03 |

Penetration Analysis

The transdermal delivery system containing either marine collagen or native collagen was applied to the human cadaver skin and the cellulose acetate skin model systems. The penetration studies were performed in a diffusion chamber and the results were recorded at 10 minutes, 30 minutes and an hour later. Sections of skin or cellulose acetate were stained with a collagen specific dye and a light microscope was used to visualize the transported collagen. TABLE 21 provides the results of these experiments. Note, that the native collagen appeared to penetrate the skin in less time than the marine collagen. This may be due to the differing concentrations of collagen used in the transdermal delivery systems (i.e., the concentration of the native collagen was 0.40 mg/ml and the concentration of the marine collagen was 1.14 mg/ml). Nevertheless, by one hour, almost all of both types of collagen had penetrated the skin in the model systems employed.

TABLE 21

| Product | Percent Penetration as per time interval | | | |
|---|---|---|---|---|
| Hydroderm | 10 minutes | 20 minutes | 30 minutes | 60 minutes |
| Marine Collagen Vial A | | | | |
| Sample A1 | 40% | 60% | 75% | 95% |
| Sample A2 | 40% | 60% | 75% | 95% |
| Sample A3 | 40% | 60% | 75% | 95% |
| Marine Collagen Vial B | | | | |
| Sample B1 | 40% | 60% | 75% | 95% |
| Sample B1 | 40% | 60% | 75% | 95% |
| Sample B1 | 40% | 60% | 75% | 95% |
| Marine collagen Vial C | | | | |
| Sample C1 | 40% | 60% | 75% | 95% |
| Sample C1 | 40% | 60% | 75% | 95% |
| Sample C1 | 40% | 60% | 75% | 95% |

TABLE 21-continued

| Product | Percent Penetration as per time interval | | | |
|---|---|---|---|---|
| Hydroderm | 10 minutes | 20 minutes | 30 minutes | 60 minutes |
| Native Collagen | | | | |
| Sample 1 | 80% | 95% | | |
| Sample 2 | 80% | 95% | | |
| Sample 3 | 80% | 95% | | |

When similar concentrations of native collagen and marine collagen were used in a transdermal delivery system, the native collagen and the marine collagen penetrated the upper three layers of the epidermis in approximately one hour. The marine collagen and the native collagen were localized in the upper three layers of the human cadaver epidermis using a collagen specific dye. A similar distribution of the collagen was confirmed by the cellulose acetate skin model. See TABLES 22 and 23.

TABLE 22

Penetration in the layers of the human skin Epidermis

| | Penetration of Epidermis layers of the Skin (Human Skin diffusion chamber study) | | | | |
|---|---|---|---|---|---|
| | Stratum Corneum | Stratum lucidum | Stratum Granulosum | Stratum Spinosum | Stratum Basale |
| Marine Vial A collagen | | | | | |
| Sample A1 | ✓ | ✓ | ✓ | — | — |
| Sample A2 | ✓ | ✓ | ✓ | — | — |
| Sample A3 | ✓ | ✓ | ✓ | — | — |
| Marine collagen Vial B | | | | | |
| Sample B1 | ✓ | ✓ | ✓ | — | — |
| Sample B1 | ✓ | ✓ | ✓ | — | — |
| Sample B1 | ✓ | ✓ | ✓ | — | — |
| Marine collagen Vial C | | | | | |
| Sample C1 | ✓ | ✓ | ✓ | — | — |
| Sample C1 | ✓ | ✓ | ✓ | — | — |
| Sample C1 | ✓ | ✓ | ✓ | — | — |
| Native collagen | | | | | |
| Sample 1 | ✓ | ✓ | ✓ | — | — |
| Sample 2 | ✓ | ✓ | ✓ | — | — |
| Sample 3 | ✓ | ✓ | ✓ | — | — |

Note:
(✓) indicates the presence of the product in the above layers of the epidermis as determined by collagen specific staining observed by light microscopy after one hour of product application.
(—) indicates absence of products in these layers of the epidermis.

TABLE 23

Penetration Hydroderm in Epidermis layers of the Skin (Cellulose Acetate model skin diffusion chamber study)

| | Stratum Corneum | Stratum lucidum | Stratum Granulosum | Stratum Spinosum | Stratum Basale |
|---|---|---|---|---|---|
| Marine collagen Vial A | | | | | |
| Sample A1 | ✓ | ✓ | ✓ | — | — |
| Sample A2 | ✓ | ✓ | ✓ | — | — |
| Sample A3 | ✓ | ✓ | ✓ | — | — |

TABLE 23-continued

Penetration Hydroderm in Epidermis layers of the Skin
(Cellulose Acetate model skin diffusion chamber study)

| | Stratum Corneum | Stratum lucidum | Stratum Granulosum | Stratum Spinosum | Stratum Basale |
|---|---|---|---|---|---|
| Marine collagen Vial B | | | | | |
| Sample B1 | ✓ | ✓ | ✓ | — | — |
| Sample B1 | ✓ | ✓ | ✓ | — | — |
| Sample B1 | ✓ | ✓ | ✓ | — | — |
| Marine collagen Vial C | | | | | |
| Sample C1 | ✓ | ✓ | ✓ | — | — |
| Sample C1 | ✓ | ✓ | ✓ | — | — |
| Sample C1 | ✓ | ✓ | ✓ | — | — |
| Native Collagen | | | | | |
| Sample 1 | ✓ | ✓ | ✓ | — | — |
| Sample 2 | ✓ | ✓ | ✓ | — | — |
| Sample 3 | ✓ | ✓ | ✓ | — | — |

Note:
(✓) indicates the presence of the product in the above layers of the epidermis as determined by collagen specific staining observed by light microscopy after one hour of product application.
(—) indicates absence of products in these layers of the epidermis.

Spectrophotometric Analysis

Spectrophotometric analysis of the diffused material revealed that the transdermal delivery system enabled significant transport of both types of collagens. See TABLE 24.

TABLE 24

| | Spectral Absorbance at wavelength 280 nm | |
|---|---|---|
| Sample number | Native type 1 collagen | Marine type 1 collagen |
| Sample 1 | 2.35 | 2.832 |
| Sample 2 | 2.766 | 2.772 |
| Sample 3 | 2.751 | 2.683 |
| Average | 2.622 | 2.762 |
| Standard error | 0.136 | 0.043 |
| Variance | 0.0557 | 0.0056 |
| Standard deviation | 0.24 | 0.07 |

Electrophoresis Analysis

A portion of the diffused material was then separated by electrophoresis and visualized by staining with a collagen-specific dye. The penetrated marine collagen remained intact during and after the analysis because the labeled marine collagen detected in the diffused material was observed to have the same molecular weight as marine collagen that had not undergone the analysis (control sample). The results showed that the marine collagen prior to the penetration study and after the penetration study maintained its molecular structure around 500 kilodaltons (KD). The native collagen also maintained a molecular weight around 500 KD before and after penetration of the epidermis, demonstrating that the native collagen that was delivered by the transdermal delivery system, like the marine collagen, remained intact into the epidermis.

Immunoprecipitation Analysis

When the transdermal delivery system containing marine collagen was immunoprecipitated using polyclonal antibodies specific for collagens types 1-7 before and after the penetration study, more evidence that the marine collagen remained in tact after the transdermal delivery was obtained. Immuno-diffusion studies verified that the marine collagen prior to penetration of the skin and post penetration of skin consisted mainly of type I collagen. This further confirmed that the collagen remained intact post penetration.

The penetration study described above provided strong evidence that the transdermal delivery systems described herein are effective at transporting high molecular weight molecules to skin cells. It was found, for example, that marine collagen type 1 (~500 kD) effectively penetrated the upper 3 layers of the epidermis and remained intact within an hour. These findings were supported by histology, spectrophotometric analysis, electrophoretic separation analysis, immunoprecipitation analysis, and immuno-diffusion analysis. The following example describes a clinical study that was performed, which verified that the transdermal delivery systems described herein effectively reduce wrinkles and improve skin tone in humans in need thereof.

EXAMPLE 6

A clinical study was performed to evaluate the ability of a transdermal delivery system containing collagen, prepared as described herein, to reduce wrinkles and fine lines and otherwise restore skin tone to subjects in need thereof. The medial half of the facial region including the neck and the upper chest areas were assigned as the regions under investigation. During a subject's routine application of the product, three times a day, digital pictures were taken at days 0, 3, 7, 14 and 21 of the regions under investigation of the face including the symmetrical region of the face where the product was not applied. Micrometer measurements of the wrinkles were then made from the digital pictures and also from the facial areas under investigation.

Subjects invited to participate in the study had facial wrinkles and were 25 years or older. Non-facial wrinkle individuals were also invited and served as the control group. The source of subjects for the study was randomly selected from the ethnically diverse population group ages ranging from 25 years to 88 years old.

TABLE 25

Description of the subjects participating in the study

| Identification Number | Gender | Ethnicity | Age | General Description |
|---|---|---|---|---|
| F101601 | Female | Hispanic American | 88 | Distinct facial wrinkles |
| F101602 | Female | Hispanic American | 67 | Distinct facial wrinkles |
| F101603 | Female | Hispanic American | 25 | Distinct facial wrinkles around the eyes |
| F101604 | Female | Caucasian | 28 | Distinct facial wrinkles around the eye region |
| M101605 | Male | Asian | 40 | Distinct facial wrinkles around the eye region |

Subjects that signed the study consent form received 30 mls of a transdermal delivery system comprising marine collagen. Micrometer measurement of the wrinkles were performed using a 10× magnification objective eye piece. The measurements were recorded and tabulated together with the digital photographs before and after application of the product. The wrinkle measurements were determined within the 3-week duration of the study. The tabulated results provided in TABLE 26, which indicates the general observations by subjects utilizing the product, and TABLE 27, which shows the wrinkle measurements. TABLE 28 shows the average percent of wrinkle reduction data generated after 21 days of application of the transdermal delivery system comprising collagen.

TABLE 26

| Identification Number | Days of product application on one half of the face including the upper chest and neck regions | | | |
|---|---|---|---|---|
| | Day 3 | Day 7 | Day 14 | Day 21 |
| F101601 | Skin felt soft, and clear, when compared to the other half without product application, slight burning sensation for 3-5 minutes upon product application. | The right half of the face cleared up and felt smooth, the slight burning sensation was still present for 3-5 minutes. | The right half of the face cleared up and felt smooth, the slight burning sensation no longer present. | The right half of the face cleared up and felt smooth, the slight burning sensation no longer present. |
| F101602 | Skin felt soft, and clear, when compared to the other half without product application, slight burning sensation for 3-5 minutes upon product application. | The right half of the face cleared up and felt smooth, the slight burning sensation was still present for 3-5 minutes. | The right half of the face cleared up and felt smooth, the slight burning sensation no longer present. | The right half of the face cleared up and felt smooth, the slight burning sensation no longer present. |
| F101603 | Skin felt soft, and clear, when compared to the other half without product application, slight burning sensation for 3-5 minutes upon product application. | The right half of the face cleared up and felt smooth, the slight burning sensation was still present for 3-5 minutes. | The right half of the face cleared up and felt smooth, the slight burning sensation no longer present. | The right half of the face cleared up and felt smooth, the slight burning sensation no longer present.. |
| F101604 | Skin felt soft, and clear, when compared to the other half without product application, slight burning sensation for 3-5 minutes upon product application. | The skin felt smooth and very soft in the facial region where product was applied. | Developed rashes in the neck region, stopped using product. | The rashes cleared up, and the skin had normal appearance as the other half in which the product was not applied. |
| M101605 | Skin felt soft, and clear, when compared to the other half without product application, slight burning sensation for 3-5 minutes upon product application. | The right half of the face cleared up and felt smooth, the slight burning sensation was still present for 3-5 minutes. | The right half of the face cleared up and felt smooth, the slight burning sensation still present for 3-5 minutes. | The right half of the face cleared up and felt smooth, the slight burning sensation still present for 3-5 minutes. |

TABLE 27

| Subject's Identification Number | Regions of the face | Average wrinkle measurements with product application on one half of the face including the upper chest and neck areas in μm | | | | | |
|---|---|---|---|---|---|---|---|
| | | Day 0 | Day 3 | Day 5 | Day 7 | Day 14 | Day 21 |
| F101601 | Around eyes | 6 μm | 6 μm | 6 μm | 5 μm | 4.5 μm | 4.5 μm |
| | Temporal cheek | 7 μm | 7 μm | 7 μm | 7 μm | 6 μm | 5.5 μm |
| | Chin | 7.5 μm | 7.5 μm | 7.5 μm | 7.5 μm | 7.0 μm | 6.5 μm |
| | Around mouth | 6.5 μm | 6.5 μm | 6.5 μm | 6.5 μm | 6.0 μm | 5.5 μm |
| F101602 | Around eyes | 3.5 μm | 3.5 μm | 3.5 μm | 3.5 μm | 3.5 μm | 3.2 μm |
| | Temporal cheek | 4.1 μm | 4.1 μm | 4.1 μm | 4.1 μm | 3.9 μm | 3.5 μm |

TABLE 27-continued

| Subject's | Average wrinkle measurements with product application on one half of the face including the upper chest and neck areas in μm | | | | | |
|---|---|---|---|---|---|---|
| Identification Number | Regions of the face | Day 0 | Day 3 | Day 5 | Day 7 | Day 14 | Day 21 |
| | Chin | 2.5 μm | 2.5 μm | 2.5 μm | 2.5 μm | 2.0 μm | 2.0 μm |
| | Around mouth | 2.0 μm | 2.0 μm | 2.0 μm | 2.0 μm | 2.0 μm | 2.0 μm |
| F101603 | Around eyes | 1.5 μm | 1.5 μm | 1.5 μm | 1.5 μm | 1.5 μm | 1.2 μm |
| | Temporal cheek | 1.0 μm | 1.0 μm | 1.0 μm | 1.0 μm | 1.0 μm | 1.0 μm |
| | Chin | 0.9 μm | 0.9 μm | 0.9 μm | 0.9 μm | 0.9 μm | 0.85 μm |
| | Around mouth | 0.5 μm | 0.5 μm | 0.5 μm | 0.5 μm | 0.5 μm | 0.45 μm |
| F101604 | Around eyes | 0.2 μm | 0.2 μm | 0.2 μm | 0.2 μm | 0.2 μm | ** |
| | Temporal cheek | 1.5 μm | 1.5 μm | 1.5 μm | 1.5 μm | 1.5 μm | ** |
| | Chin | 1.0 μm | 1.0 μm | 1.0 μm | 1.0 μm | 1.0 μm | ** |
| | Around mouth | 0.5 μm | 0.5 μm | 0.5 μm | 0.5 μm | 0.5 μm | ** |
| M101605 | Around eyes | 1.5 μm | 1.5 μm | 1.5 μm | 1.5 μm | 1.5 μm | 1.0 μm |
| | Temporal cheek | 0.5 μm | 0.5 μm | 0.5 μm | 0.5 μm | 0.5 μm | 0.3 μm |
| | Chin | 1.0 μm | 1.0 μm | 1.0 μm | 1.0 μm | 1.0 μm | 0.9 μm |
| | Around mouth | 1.5 μm | 1.5 μm | 1.5 μm | 1.5 μm | 1.5 μm | 1.2 μm |

Note
** Indicates the subject stopped using the product.

TABLE 28

| Subject's | The percent reduction of wrinkle measurement on the regions of the face at day 21 of Hydroderm product application | | | |
|---|---|---|---|---|
| Identification Number | Around eyes | Temporal cheek | Chin | Around mouth |
| F101601 | 25% | 21.4% | 13.3% | 15.4% |
| F101602 | 8.6% | 14.6% | 20.0% | 0.0% |
| F101603 | 20.0% | 0.0% | 5.6% | 10.0% |
| F101604 | 0.0% | 0.0% | 0.0% | 0.0% |
| M101605 | 33.3% | 40.0% | 10% | 20.0% |
| Average % | 17.42% | 15.20% | 9.78% | 9.08% |
| Overall effectiveness | On the entire facial region where the product was applied. | | | 10.29% |

The data generated from this study indicates that the overall effectiveness of transdermal delivery system comprising marine collagen as a wrinkle reducer is 10.29% when applied twice daily for 21 days. As indicated by Table 28, the percent reduction of the wrinkles varies with the various areas of the face where it is applied, with 17.4% reduction around the eye regions and 15.20% at the temporal cheeks at the high end and around 9% at the chin and mouth regions. The next example sets forth experiments that demonstrate that transdermal delivery systems containing ethoxylated oils of less than 20 ethoxylations/molecule transfer a delivered agent to the skin more effectively than transdermal delivery systems containing ethoxylated oils of 20 or more ethoxylations/molecule.

EXAMPLE 7

Several transdermal delivery system formulations containing collagen (1.2 mg/ml) and an ethoxylated oil having different amounts of ethoxylations/molecule are prepared. Formulations containing ethoxylated oil of either 12, 16, 18, 20, 24, and 30 ethoxylations/molecule, water, and marine collagen (1.2 mg/ml) are made. Approximately 0.5 ml of each of these formulations are applied to human cadaver skin in a diffusion chamber and the penetration of collagen is monitored over time (e.g., 10 minutes, 30 minutes, 45 minutes and one hour). Sections of the skin are taken, stained with a collagen specific dye, and the stained sections are analyzed under a light microscope.

A greater amount of collagen-specific staining will be seen in stained skin sections collected at the various time points with formulations containing less than 20 ethoxylations/molecule than with formulations containing 20 or more ethoxylations/molecule. Formulations containing less than 20 ethoxylations/molecule will also penetrate the skin faster than formulations containing 20 or more ethoxylations/molecule.

In a second set of experiments, the collagen that has penetrated the skin at the various time points above is collected from the diffusion chamber and analyzed in a spectrophotometer. As above, a greater amount of collagen will be detected in samples collected at the various time points with formulations containing less than 20 ethoxylations/molecule than formulations containing 20 or more ethoxylations/molecule. Formulations containing less than 20 ethoxylations/molecule will also be observed to penetrate the skin faster than formulations containing 20 or more ethoxylations/molecule.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. A method of reducing the appearance of a varicose vein or a spider vein comprising:
   providing a transdermal delivery system that comprises an ethoxylated oil containing between 10 and 19 ethoxylations/molecule; and
   applying said transdermal delivery system to said varicose vein or said spider vein.

2. A method of reducing the appearance of a stretch mark comprising:
   providing a transdermal delivery system that comprises an ethoxylated oil containing between 10 and 19 ethoxylations/molecule; and
   applying said transdermal delivery system to said stretch mark.

3. The method of claim 2, wherein the transdermal delivery system further comprises Kayuuputih Eucalyptus oil.

4. A transdermal delivery system comprising:
   an ethoxylated oil containing between 10 and 19 ethoxylations/molecule; and
   Kayuuputih Eucalyptus oil mixed with said ethoxylated oil.

5. A method of reducing the appearance of a skin discoloration comprising:
   providing a transdermal delivery system that comprises an ethoxylated oil containing between 10 and 19 ethoxylations/molecule and a skin brightener; and
   applying said transdermal delivery system to said skin discoloration.

6. The method of claim 5, wherein the skin brightener is a melanin inhibitor.

7. The method of claim 5, wherein the skin brightener is a tyrosinase inhibitor.

8. The method of claim 5, wherein the skin brightener is Melaslow.

9. The method of claim 5, wherein the skin brightener is Etioline.

10. A transdermal delivery system comprising:
    an ethoxylated oil containing between 10 and 19 ethoxylations/molecule; and
    a skin brightener mixed with said ethoxylated oil.

11. The transdermal delivery system of claim 10, wherein the skin brightener is a melanin inhibitor.

12. The transdermal delivery system of claim 10, wherein the skin brightener is a tyrosinase inhibitor.

13. The transdermal delivery system of claim 10, wherein the skin brightener is Melaslow.

14. The transdermal delivery system of claim 10, wherein the skin brightener is Etioline.

15. A method of providing a fragrance comprising:
    providing a transdermal delivery system that comprises an ethoxylated oil containing between 10 and 19 ethoxylations/molecule and a fragrance; and
    applying said transdermal delivery system to the skin of an individual.

16. A transdermal delivery system comprising:
    an ethoxylated oil containing between 10 and 19 ethoxylations/molecule; and
    a fragrance mixed with said ethoxylated oil.

17. A method of facilitating recovery from a burn comprising:
    providing a transdermal delivery system that comprises an ethoxylated oil containing between 10 and 19 ethoxylations/molecule; and
    applying said transdermal delivery system to a burn.

18. The method of claim 1, wherein said ethoxylated oil contains 16 ethoxylations/molecule.

19. The method of claim 1, wherein said ethoxylated oil comprises an ethoxylated macadamia nut oil.

20. The method of claim 1, wherein said ethoxylated oil comprises an ethoxylated meadow foam oil.

21. The method of claim 1, wherein the transdermal delivery system further comprises water.

22. The method of claim 1, wherein the transdermal delivery system further comprises an alcohol.

23. The method of claim 2, wherein said ethoxylated oil contains 16 ethoxylations/molecule.

24. The method of claim 2, wherein said ethoxylated oil comprises an ethoxylated macadamia nut oil.

25. The method of claim 2, wherein said ethoxylated oil comprises an ethoxylated meadow foam oil.

26. The method of claim 2, wherein the transdermal delivery system further comprises water.

27. The method of claim 2, wherein the transdermal delivery system further comprises an alcohol.

28. The method of claim 2, wherein the transdermal delivery system further comprises a delivered agent.

29. The transdermal delivery system of claim 4, wherein said ethoxylated oil contains 16 ethoxylations/molecule.

30. The transdermal delivery system of claim 4, wherein said ethoxylated oil comprises an ethoxylated macadamia nut oil.

31. The transdermal delivery system of claim 4, wherein said ethoxylated oil comprises an ethoxylated meadow foam oil.

32. The transdermal delivery system of claim 4, further comprising water.

33. The transdermal delivery system of claim 4, further comprising an alcohol.

34. The transdermal delivery system of claim 4, wherein said delivered agent is less than 1,000 daltons.

35. The transdermal delivery system of claim 4, wherein said delivered agent is 1,000 daltons or greater.

36. The transdermal delivery system of claim 4, wherein said delivered agent is 10,000 daltons or greater.

37. The transdermal delivery system of claim 4, wherein said delivered agent is 100,000 daltons or greater.

38. The transdermal delivery system of claim 4, wherein said delivered agent is 300,000 daltons or greater.

39. The transdermal delivery system of claim 4, wherein said delivered agent is 500,000 daltons or greater.

40. The transdermal delivery system of claim 4, wherein said delivered agent is less than 2,000,000 daltons.

41. The transdermal delivery system of claim 4, wherein said delivered agent is a steroid.

42. The transdermal delivery system of claim 4, wherein said delivered agent is an antiviral compound.

43. The transdermal delivery system of claim 4, wherein said delivered agent is a nucleic acid.

44. The transdermal delivery system of claim 4, wherein said delivered agent is a peptide.

45. The transdermal delivery system of claim 44, wherein said peptide is less than 1,000 daltons.

46. The transdermal delivery system of claim 44, wherein said peptide is 1,000 daltons or more but less than 2,000,000 daltons.

47. The transdermal delivery system of claim 44, wherein said peptide is 100,000 daltons or greater.

48. The transdermal delivery system of claim 44, wherein said peptide is 300,000 daltons or greater.

49. The transdermal delivery system of claim 44, wherein said peptide is 500,000 daltons or greater.

50. The transdermal delivery system of claim 4, further comprising a second delivered agent, wherein said second delivered agent is a non-steroidal anti inflammatory drug (NSAID).

51. The transdermal delivery system of claim 50, wherein said non-steroidal anti inflammatory drug (NSAID) is selected from the group consisting of ibuprofen (2-(isobutylphenyl)-propionic acid); methotrexate (N-[4-(2, 4 diamino 6-pteridinyl-methyl]methylamino]benzoyl)-L-glutamic acid); aspirin (acetylsalicylic acid); salicylic acid; diphenhydramine (2-(diphenylmethoxy)-NN-dimethylethylamine hydrochloride); naproxen (2-naphthaleneacetic acid, 6-methoxy-9-methyl-, sodium salt, (−)); phenylbutazone (4-butyl-1,2-diphenyl-3,5-pyrazolidinedione); sulindac-(2)-5-fuoro-2-methyl-1-[[p-(methylsulfinyl)phenyl]methylene-]-1H-indene-3-acetic acid; diflunisal (2',4', -difluoro-4-hydroxy-3-biphenylcarboxylic acid; piroxicam (4-hydroxy-2-methyl-N-2-pyridinyl-2H-1,2-benzothiazine-2-carboxamide 1,1-dioxide, an oxicam; indomethacin (1-(4-chlorobenzoyl)-5-methoxy-2-methyl-H-indole-3-acetic acid); meclofenamate sodium (N-(2,6-dichloro-m-tolyl) anthranilic acid, sodium salt, monohydrate); ketoprofen (2-(3-benzoylphenyl)-propionic acid; tolmetin sodium (sodium 1-methyl-5-(4-methylbenzoyl-1H-pyrrole-2-acetate dihydrate); diclofenac sodium (2-[(2,6-dichlorophenyl)amino] benzeneatic acid, monosodium salt); hydroxychioroquine sulphate (2-{[4-[(7-chloro-4-quinolyl) amino]pentyl] ethylamino}ethanol sulfate (1:1); penicillamine (3-mercapto-D-valine); flurbiprofen ([1,1-biphenyl]-4-acetic acid, 2-fluoro-aphamethyl-, (+−)); cetodolac (1-8-diethyl-13,4,9, tetra hydropyrano-[3-4-13]indole-1-acetic acid; mefenamic acid (N-(2,3-xylyl)anthranilic acid; and diphenhydramine hydrochloride (2-diphenyl methoxy-N,N-di-methyl-ethamine hydrochloride).

52. The transdermal delivery system of claim 4, wherein said delivered agent is a collagen or fragment thereof.

53. The transdermal delivery system of claim 52, wherein said collagen has an approximate average molecular weight from about 2,000 daltons to about 500,000 daltons.

54. The transdermal delivery system of claim 52, wherein the amount of said collagen or fragment thereof by weight or volume is 0.1% to 50.0%.

55. The transdermal delivery system of claim 52, wherein said collagen or fragment thereof has an approximate average molecular weight of about 2,000 daltons and the therapeutically effective amount by weight or volume is 0.1% to 50.0%.

56. The transdermal delivery system of claim 52, wherein said collagen or fragment thereof has an approximate average molecular weight of about 300,000 daltons and the therapeutically effective amount is 0.1% to 2.0%.

57. The transdermal delivery system of claim 52, wherein said collagen or fragment thereof has an approximate average molecular weight of about 500,000 daltons and the therapeutically effective amount by weight or volume is 0.1% to 4.0%.

58. A method of transdermal delivery of a delivered agent comprising:
    identifying a subject in need of transdermal delivery of a delivered agent; and
    providing said subject a transdermal delivery system according to claim 4.

59. The method of claim 58, wherein said ethoxylated oil contains 16 ethoxylations/molecule.

60. The method of claim 58, wherein said ethoxylated oil comprises an ethoxylated macadamia nut oil.

61. The method of claim 58, wherein said ethoxylated oil comprises an ethoxylated meadow foam oil.

62. The method of claim 58, further comprising water.

63. The method of claim 58, further comprising an alcohol.

64. The method of claim 58, wherein said delivered agent is less than 1,000 daltons.

65. The method of claim 58, wherein said delivered agent is 1,000 daltons or greater.

66. The method of claim 58, wherein said delivered agent is 10,000 daltons or greater.

67. The method of claim 58, wherein said delivered agent is 100,000 daltons or greater.

68. The method of claim 58, wherein said delivered agent is 300,000 daltons or greater.

69. The method of claim 58, wherein said delivered agent is 500,000 daltons or greater.

70. The method of claim 58, wherein said delivered agent is less than 2,000,000 daltons.

71. The method of claim 58, wherein said delivered agent is a steroid.

72. The method of claim 58, wherein said delivered agent is an antiviral compound.

73. The method of claim 58, wherein said delivered agent is a nucleic acid.

74. The method of claim 58, wherein said delivered agent is a peptide.

75. The method of claim 74, wherein said peptide is less than 1,000 daltons.

76. The method of claim 74, wherein said peptide is 1,000 daltons or more but less than 2,000,000 daltons.

77. The method of claim 74, wherein said peptide is 100,000 daltons or greater.

78. The method of claim 74, wherein said peptide is 300,000 daltons or greater.

79. The method of claim 74, wherein said peptide is 500,000 daltons or greater.

80. The method of claim 58, further comprising a second delivered agent, wherein said second delivered agent is a non-steroidal anti inflammatory drug (NSAID).

81. The method of claim 80, wherein said non-steroidal anti inflammatory drug (NSAID) is selected from the group consisting of ibuprofen (2-(isobutylphenyl)-propionic acid); methotrexate (N-[4-(2,4 diamino 6-pteridinyl-methyl]methylamino]benzoyl)-L-glutamic acid); aspirin (acetylsalicylic acid); salicylic acid; diphenhydramine (2-(diphenylmethoxy)-NN-dimethylethylamine hydrochloride); naproxen (2-naphthaleneacetic acid, 6-methoxy-9-methyl-, sodium salt, (−)); phenylbutazone (4-butyl -1,2-diphenyl-3, 5-pyrazolidinedione); sulindac-(2)-5-fuoro-2-methyl-1-[[p-(methylsulfinyl)phenyl]methylene-]-1H-indene-3-acetic acid; diflunisal (2',4'-difluoro-4-hydroxy-3-biphenylcarboxylic acid; piroxicam (4-hydroxy-2-methyl-N-2-pyridinyl-2H-1, 2-benzothiazine-2-carboxamide 1,1-dioxide, an oxicam; indomethacin (1-(4-chlorobenzoyl)-5-methoxy-2-methyl-H-indole-3-acetic acid); meclofenamate sodium (N - (2,6-dichloro-m-tolyl) anthranilic acid, sodium salt, monohydrate); ketoprofen (2-(3-benzoylphenyl)-propionic acid; tolmetin sodium (sodium 1-methyl-5-(4-methylbenzoyl - 1H-pyrrole-2-acetate dihydrate); diclofenac sodium (2-[(2, 6-dichlorophenyl)amino]benzeneatic acid, monosodium salt); hydroxychloroquine sulphate (2-{[4-[(7-chloro-4-quinolyl) amino]pentyl]ethylamino}ethanol sulfate (1:1); penicillamine (3-mercapto-D -valine); flurbiprofen ([1,1-biphenyl]-4-acetic acid, 2-fluoro-alphamethyl-, (+−)); cetodolac (1-8-diethyl-13,4,9, tetra hydropyrano-[3-4-13]indole-1-acetic acid; mefenamic acid (N -(2,3-xylyl)anthranilic acid; and diphenhydramine hydrochloride (2-diphenyl methoxy-N, N-di-methylethamine hydrochloride).

82. The method of claim 58, wherein said delivered agent is a collagen or fragment thereof.

83. The method of claim 82, wherein said collagen has an approximate average molecular weight from about 2,000 daltons to about 500,000 daltons.

84. The method of claim 82, wherein the amount of said collagen or fragment thereof by weight or volume is 0.1% to 50.0%.

85. The method of claim 82, wherein said collagen or fragment thereof has an approximate average molecular weight of about 2,000 daltons and the therapeutically effective amount by weight or volume is 0.1% to 50.0%.

86. The method of claim 82, wherein said collagen or fragment thereof has an approximate average molecular weight of about 300,000 daltons and the therapeutically effective amount is 0.1% to 2.0%.

87. The method of claim 82, wherein said collagen or fragment thereof has an approximate average molecular weight of about 500,000 daltons and the therapeutically effective amount by weight or volume is 0.1% to 4.0%.

88. The method of claim 5, wherein said ethoxylated oil contains 16 ethoxylations/molecule.

89. The method of claim 5, wherein said ethoxylated oil comprises an ethoxylated macadamia nut oil.

90. The method of claim 5, wherein said ethoxylated oil comprises an ethoxylated meadow foam oil.

91. The method of claim 5, further comprising water.

92. The method of claim 5, further comprising an alcohol.

93. The method of claim 5, further comprising a second delivered agent, wherein said second delivered agent is a peptide.

94. The method of claim 93, wherein said peptide is less than 1,000 daltons.

95. The method of claim 93, wherein said peptide is 1,000 daltons or more but less than 2,000,000 daltons.

96. The method of claim 93, wherein said peptide is 100,000 daltons or greater.

97. The method of claim 93, wherein said peptide is 300,000 daltons or greater.

98. The method of claim 93, wherein said peptide is 500,000 daltons or greater.

99. The method of claim 93, wherein said second delivered agent is a collagen or fragment thereof.

100. The method of claim 99, wherein said collagen has an approximate average molecular weight from about 2,000 daltons to about 500,000 daltons.

101. The method of claim 99, wherein the amount of said collagen or fragment thereof by weight or volume is 0.1% to 50.0%.

102. The method of claim 99, wherein said collagen or fragment thereof has an approximate average molecular weight of about 2,000 daltons and the therapeutically effective amount by weight or volume is 0.1% to 50.0%.

103. The method of claim 99, wherein said collagen or fragment thereof has an approximate average molecular weight of about 300,000 daltons and the therapeutically effective amount is 0.1% to 2.0%.

104. The method of claim 99, wherein said collagen or fragment thereof has an approximate average molecular weight of about 500,000 daltons and the therapeutically effective amount by weight or volume is 0.1% to 4.0%.

105. The transdermal delivery system of claim 10, wherein said ethoxylated oil contains 16 ethoxylations/molecule.

106. The transdermal delivery system of claim 10, wherein said ethoxylated oil comprises an ethoxylated macadamia nut oil.

107. The transdermal delivery system of claim 10, wherein said ethoxylated oil comprises an ethoxylated meadow foam oil.

108. The transdermal delivery system of claim 10, further comprising water.

109. The transdermal delivery system of claim 10, further comprising an alcohol.

110. The transdermal delivery system of claim 10, further comprising a second delivered agent, wherein said second delivered agent is a peptide.

111. The transdermal delivery system of claim 110, wherein said peptide is less than 1,000 daltons.

112. The transdermal delivery system of claim 110, wherein said peptide is 1,000 daltons or more but less than 2,000,000 daltons.

113. The transdermal delivery system of claim 112, wherein said peptide is 100,000 daltons or greater.

114. The transdermal delivery system of claim 112, wherein said peptide is 300,000 daltons or greater.

115. The transdermal delivery system of claim 112, wherein said peptide is 500,000 daltons or greater.

116. The transdermal delivery system of claim 112, wherein said second delivered agent is a collagen or fragment thereof.

117. The transdermal delivery system of claim 116, wherein said collagen has an approximate average molecular weight from about 2,000 daltons to about 500,000 daltons.

118. The transdermal delivery system of claim 116, wherein the amount of said collagen or fragment thereof by weight or volume is 0.1% to 50.0%.

119. The transdermal delivery system of claim 116, wherein said collagen or fragment thereof has an approximate average molecular weight of about 2,000 daltons and the therapeutically effective amount by weight or volume is 0.1% to 50.0%.

120. The transdermal delivery system of claim 116, wherein said collagen or fragment thereof has an approximate average molecular weight of about 300,000 daltons and the therapeutically effective amount is 0.1% to 2.0%.

121. The transdermal delivery system of claim 116, wherein said collagen or fragment thereof has an approximate average molecular weight of about 500,000 daltons and the therapeutically effective amount by weight or volume is 0.1% to 4.0%.

122. The method of claim 15, wherein said ethoxylated oil contains 16 ethoxylations/molecule.

123. The method of claim 15, wherein said ethoxylated oil comprises an ethoxylated macadamia nut oil.

124. The method of claim 15, wherein said ethoxylated oil comprises an ethoxylated meadow foam oil.

125. The method of claim 15, further comprising water.

126. The method of claim 15, further comprising an alcohol.

127. The method of claim 15, further comprising a delivered agent other than said fragrance.

128. The method of claim 127, wherein said delivered agent is less than 1,000 daltons.

129. The method of claim 127, wherein said delivered agent is 1,000 daltons or greater.

130. The method of claim 127, wherein said delivered agent is 10,000 daltons or greater.

131. The method of claim 127, wherein said delivered agent is 100,000 daltons or greater.

132. The method of claim 127, wherein said delivered agent is 300,000 daltons or greater.

133. The method of claim 127, wherein said delivered agent is 500,000 daltons or greater.

134. The method of claim 127, wherein said delivered agent is less than 2,000,000 daltons.

135. The method of claim 127, wherein said delivered agent is a steroid.

136. The method of claim 127, wherein said delivered agent is an antiviral compound.

137. The method of claim 127, wherein said delivered agent is a nucleic acid.

138. The method of claim 127, wherein said delivered agent is a peptide.

139. The method of claim 138, wherein said peptide is less than 1,000 daltons.

140. The method of claim 138, wherein said peptide is 1,000 daltons or more but less than 2,000,000 daltons.

141. The method of claim 138, wherein said peptide is 100,000 daltons or greater.

142. The method of claim 138, wherein said peptide is 300,000 daltons or greater.

143. The method of claim 138, wherein said peptide is 500,000 daltons or greater.

144. The method of claim 127, wherein said delivered agent is a non-steroidal anti inflammatory drug (NSAID).

145. The method of claim 144, wherein said non-steroidal anti inflammatory drug (NSAID) is selected from the group consisting of ibuprofen (2-(isobutylphenyl)-propionic acid); methotrexate (N-[4-(2,4 diamino 6-pteridinyl-methyl]methylamino]benzoyl)-L-glutamic acid); aspirin (acetylsalicylic acid); salicylic acid; diphenhydramine (2-(diphenylmethoxy)-NN-dimethylethylamine hydrochloride); naproxen (2-naphthaleneacetic acid, 6-methoxy-9-methyl-, sodium salt, (−)); phenylbutazone (4-butyl -1,2-diphenyl-3, 5-pyrazolidinedione); sulindac-(2)-5-fuoro-2-methyl-1-[[p-(methylsulfinyl)phenyl]methylene-]-1H-indene-3-acetic acid; diflunisal (2',4', -difluoro-4-hydroxy-3-biphenylcarboxylic acid; piroxicam (4-hydroxy-2-methyl-N-2-pyridinyl-2H-1, 2-benzothiazine-2-carboxamide 1,1-dioxide, an oxicam; indomethacin (1-(4-chlorobenzoyl)-5-methoxy-2-methyl-H-indole-3-acetic acid); meclofenamate sodium (N -(2,6-dichloro-m-tolyl) anthranilic acid, sodium salt, monohydrate); ketoprofen (2-(3-benzoylphenyl)-propionic acid; tolmetin sodium (sodium 1-methyl-5-(4-methylbenzoyl-1H-pyrrole-2-acetate dihydrate); diclofenac sodium (2-[(2,6-dichlorophenyl)amino]benzeneatic acid, monosodium salt); hydroxychloroquine sulphate (2-{[4-[(7-chloro-4-quinolyl)amino]pentyl]ethylamino}ethanol sulfate (1:1); penicillamine (3-mercapto-D-valine); flurbiprofen ([1,1-biphenyl]-4-acetic acid, 2-fluoro-alphamethyl-, (+−)); cetodolac (1-8-diethyl-13,4,9, tetra hydropyrano-[3-4-13]indole-1-acetic acid; mefenamic acid (N-(2,3-xylyl)anthranilic acid; and diphenhydramine hydrochloride (2-diphenyl methoxy-N, N-di-methylethamine hydrochloride).

146. The method of claim 127, wherein said delivered agent is a collagen or fragment thereof.

147. The method of claim 146, wherein said collagen has an approximate average molecular weight from about 2,000 daltons to about 500,000 daltons.

148. The method of claim 146, wherein the amount of said collagen or fragment thereof by weight or volume is 0.1% to 50.0%.

149. The method of claim 146, wherein said collagen or fragment thereof has an approximate average molecular weight of about 2,000 daltons and the therapeutically effective amount by weight or volume is 0.1% to 50.0%.

150. The method of claim 146, wherein said collagen or fragment thereof has an approximate average molecular weight of about 300,000 daltons and the therapeutically effective amount is 0.1% to 2.0%.

151. The method of claim 146, wherein said collagen or fragment thereof has an approximate average molecular weight of about 500,000 daltons and the therapeutically effective amount by weight or volume is 0.1% to 4.0%.

152. The method of claim 15, wherein said fragrance is selected from the group consisting of lemon, lavender, orange, tangerine, and Y-Lang Y-Lang.

153. The transdermal delivery system of claim 16, wherein said ethoxylated oil contains 16 ethoxylations/molecule.

154. The transdermal delivery system of claim 16, wherein said ethoxylated oil comprises an ethoxylated macadamia nut oil.

155. The transdermal delivery system of claim 16, wherein said ethoxylated oil comprises an ethoxylated meadow foam oil.

156. The transdermal delivery system of claim 16, further comprising water.

157. The transdermal delivery system of claim 16, further comprising an alcohol.

158. The transdermal delivery system of claim 16, further comprising a delivered agent other than said fragrance.

159. The transdermal delivery system of claim 158, wherein said delivered agent is less than 1,000 daltons.

160. The transdermal delivery system of claim 158, wherein said delivered agent is 1,000 daltons or greater.

161. The transdermal delivery system of claim 158, wherein said delivered agent is 10,000 daltons or greater.

162. The transdermal delivery system of claim 158, wherein said delivered agent is 100,000 daltons or greater.

163. The transdermal delivery system of claim 158, wherein said delivered agent is 300,000 daltons or greater.

164. The transdermal delivery system of claim 158, wherein said delivered agent is 500,000 daltons or greater.

165. The transdermal delivery system of claim 158, wherein said delivered agent is less than 2,000,000 daltons.

166. The transdermal delivery system of claim 158, wherein said delivered agent is a steroid.

167. The transdermal delivery system of claim 158, wherein said delivered agent is an antiviral compound.

168. The transdermal delivery system of claim 158, wherein said delivered agent is a nucleic acid.

169. The transdermal delivery system of claim 158, wherein said delivered agent is a peptide.

170. The transdermal delivery system of claim 169, wherein said peptide is less than 1,000 daltons.

171. The transdermal delivery system of claim 169, wherein said peptide is 1,000 daltons or more but less than 2,000,000 daltons.

172. The transdermal delivery system of claim 169, wherein said peptide is 100,000 daltons or greater.

173. The transdermal delivery system of claim 169, wherein said peptide is 300,000 daltons or greater.

174. The transdermal delivery system of claim 169, wherein said peptide is 500,000 daltons or greater.

175. The transdermal delivery system of claim 158, wherein said delivered agent is a non-steroidal anti inflammatory drug (NSAID).

176. The transdermal delivery system of claim 175, wherein said non-steroidal anti inflammatory drug (NSAID) is selected from the group consisting of ibuprofen (2-(isobutylphenyl)-propionic acid); methotrexate (N-[4-(2,4 diamino 6-pteridinyl -methyl]methylamino]benzoyl)-L-glutamic acid); aspirin (acetylsalicylic acid); salicylic acid; diphenhydramine (2-(diphenylmethoxy)-NN-dimethylethylamine hydrochloride); naproxen (2-naphthaleneacetic acid, 6-methoxy-9-methyl-, sodium salt, (–)); phenylbutazone (4-butyl-1,2-diphenyl-3,5-pyrazolidinedione); sulindac-(2)-5-fuoro-2-methyl-1-[[p-(methylsulfinyl)phenyl]methylene-]-1H-indene-3-acetic acid; diflunisal (2',4'-difluoro-4-hydroxy-3-biphenylcarboxylic acid; piroxicam (4-hydroxy-2-methyl-N-2-pyridinyl-2H-1,2-benzothiazine-2-carboxamide 1,1-dioxide, an oxicam; indomethacin (1-(4-chlorobenzoyl)-5-methoxy-2-methyl-H-indole-3-acetic acid); meclofenamate sodium (N-(2,6-dichloro-m-tolyl) anthranilic acid, sodium salt, monohydrate); ketoprofen (2-(3-benzoylphenyl)-propionic acid; tolmetin sodium (sodium 1-methyl-5-(4-methylbenzoyl-1H-pyrrole-2-acetate dihydrate); diclofenac sodium (2-[(2,6-dichlorophenyl)amino] benzeneatic acid, monosodium salt); hydroxychloroquine sulphate (2-{[4-[(7-chloro-4-quinolyl) amino]pentyl] ethylamino}ethanol sulfate (1:1); penicillamine (3-mercapto-D-valine); flurbiprofen ([1,1-biphenyl]-4-acetic acid, 2-fluoro-aiphamethyl-, (+–)); cetodolac (1-8-diethyl-13,4,9, tetra hydropyrano-[3-4-13]indole-1-acetic acid; mefenamic acid (N-(2,3-xylyl)anthranilic acid; and diphenhydramine hydrochloride (2-diphenyl methoxy-N,N-di-methyl-ethamine hydrochloride).

177. The transdermal delivery system of claim 158, wherein said delivered agent is a collagen or fragment thereof.

178. The transdermal delivery system of claim 177, wherein said collagen has an approximate average molecular weight from about 2,000 daltons to about 500,000 daltons.

179. The transdermal delivery system of claim 178, wherein the amount of said collagen or fragment thereof by weight or volume is 0.1% to 50.0%.

180. The transdermal delivery system of claim 178, wherein said collagen or fragment thereof has an approximate average molecular weight of about 2,000 daltons and the therapeutically effective amount by weight or volume is 0.1% to 50.0%.

181. The transdermal delivery system of claim 178, wherein said collagen or fragment thereof has an approximate average molecular weight of about 300,000 daltons and the therapeutically effective amount is 0.1% to 2.0%.

182. The transdermal delivery system of claim 178, wherein said collagen or fragment thereof has an approximate average molecular weight of about 500,000 daltons and the therapeutically effective amount by weight or volume is 0.1% to 4.0%.

183. The transdermal delivery system of claim 16, wherein said fragrance is selected from the group consisting of lemon, lavender, orange, tangerine, and Y-Lang Y-Lang.

184. The method of claim 17, wherein said ethoxylated oil contains 16 ethoxylations/molecule.

185. The method of claim 17, wherein said ethoxylated oil comprises an ethoxylated macadamia nut oil.

186. The method of claim 17, wherein said ethoxylated oil comprises an ethoxylated meadow foam oil.

187. The method of claim 17, wherein the transdermal delivery system further comprises water.

188. The method of claim 17, wherein the transdermal delivery system further comprises an alcohol.

* * * * *

SEQUENCE LISTING

<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Wound healing peptide

<400> SEQUENCE: 1

Leu Lys Glu Glu Lys Lys
 1               5